US010973227B2

(12) United States Patent
White et al.

(10) Patent No.: US 10,973,227 B2
(45) Date of Patent: Apr. 13, 2021

(54) FREEZING AND ARCHIVING CELLS ON A MICROFLUIDIC DEVICE

(71) Applicant: BERKELEY LIGHTS, INC., Emeryville, CA (US)

(72) Inventors: Mark P. White, San Francisco, CA (US); Kevin T. Chapman, Santa Monica, CA (US); Andrew W. McFarland, Berkeley, CA (US); Eric D. Hobbs, Livermore, CA (US); Randall D. Lowe, Jr., Emeryville, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 511 days.

(21) Appl. No.: 15/136,777

(22) Filed: Apr. 22, 2016

(65) Prior Publication Data
US 2016/0338347 A1 Nov. 24, 2016

Related U.S. Application Data

(60) Provisional application No. 62/151,382, filed on Apr. 22, 2015.

(51) Int. Cl.
*A01N 1/02* (2006.01)
*C12M 1/00* (2006.01)
*B01L 3/00* (2006.01)

(52) U.S. Cl.
CPC ......... *A01N 1/0284* (2013.01); *A01N 1/0221* (2013.01); *A01N 1/0263* (2013.01); *B01L 3/502715* (2013.01); *B01L 3/502761* (2013.01); *C12M 47/04* (2013.01); *B01L 2200/0668* (2013.01); *B01L 2300/021* (2013.01); *B01L 2300/024* (2013.01); *B01L 2300/0864* (2013.01); *B01L 2300/16* (2013.01); *B01L 2300/163* (2013.01); *B01L 2300/18* (2013.01); *B01L 2300/1894* (2013.01)

(58) Field of Classification Search
CPC ... A01N 1/0284; A01N 1/0268; C12M 23/16; B01L 3/5027
See application file for complete search history.

(56) References Cited

U.S. PATENT DOCUMENTS

| | | | |
|---|---|---|---|
| 6,294,063 B1 | 9/2001 | Becker | |
| 6,942,776 B2 | 9/2005 | Medoro | |
| 7,090,759 B1 | 8/2006 | Seul | |
| 7,252,928 B1 | 8/2007 | Hafeman et al. | |
| 7,612,355 B2 | 11/2009 | Wu et al. | |
| 7,699,969 B2 | 4/2010 | Manaresi | |
| 7,956,339 B2 | 6/2011 | Ohta et al. | |
| 9,464,973 B2 * | 10/2016 | Fuhr | A01N 1/00 |
| 2003/0008364 A1 | 1/2003 | Wang | |
| 2003/0224528 A1 | 12/2003 | Chiou | |
| 2004/0072278 A1 | 4/2004 | Chou | |
| 2005/0112548 A1 | 5/2005 | Segawa | |
| 2005/0175981 A1 | 8/2005 | Voldman | |
| 2006/0091015 A1 | 5/2006 | Lau | |
| 2006/0154361 A1 | 7/2006 | Wikswo | |
| 2006/0263612 A1 | 11/2006 | Chen | |
| 2007/0095669 A1 | 5/2007 | Lau | |
| 2008/0302732 A1 | 12/2008 | Soh | |
| 2009/0130750 A1 | 5/2009 | Cecchi | |
| 2010/0003666 A1 | 1/2010 | Lee | |
| 2010/0230284 A1 | 9/2010 | Stephenson | |
| 2011/0003325 A1 | 1/2011 | Durack | |
| 2011/0117634 A1 | 5/2011 | Halamish | |
| 2012/0024708 A1 | 2/2012 | Chiou | |
| 2012/0118740 A1 | 5/2012 | Garcia | |
| 2012/0184010 A1 | 7/2012 | Medoro et al. | |
| 2012/0325665 A1 | 12/2012 | Chiou | |
| 2013/0118905 A1 | 5/2013 | Morimoto | |
| 2013/0171628 A1 | 7/2013 | DiCarlo | |
| 2013/0190212 A1 | 7/2013 | Handique | |
| 2013/0204076 A1 | 8/2013 | Han | |
| 2013/0261021 A1 | 10/2013 | Bocchi | |
| 2014/0116881 A1 | 5/2014 | Chapman | |
| 2014/0124370 A1 | 5/2014 | Short et al. | |
| 2014/0154791 A1 | 6/2014 | North | |
| 2015/0151298 A1 | 6/2015 | Hobbs | |
| 2015/0151307 A1 | 6/2015 | Breinlinger | |
| 2015/0165436 A1 | 6/2015 | Chapman | |

(Continued)

FOREIGN PATENT DOCUMENTS

| | | |
|---|---|---|
| CN | 101802599 | 8/2010 |
| CN | 102427883 | 8/2014 |

(Continued)

OTHER PUBLICATIONS

John Ryan "General Guide for Cryogenically Storing Animal Cell Cultures" available at http://www.labautopedia.org/mw/General_Guide_for_Cryogenically_Storing_Animal_Cell_Cultures, 9 pages, available online on Jun. 28, 2010 (Year: 2010).*

PCT International Search Report and Written Opinion for International Appln. No. PCT/US2016/029032, Applicant Berkeley Lights, Inc., Forms PCT/ISA/210, 220, and 237, dated Oct. 18, 2016 (21 pages).

Ritchie et al., "Reconstitution of Membrane Proteins in Phospholipid Bilayer Nanodiscs," Methods Enzymol., 464:211-231 (2009), 23 pages.

(Continued)

*Primary Examiner* — Thane Underdahl
(74) *Attorney, Agent, or Firm* — Vista IP Law Group, LLP

(57) ABSTRACT

A method of processing and storing biological cells includes introducing a flowable medium into a microfluidic device, the flowable medium including biological cells; sequestering one or more biological cells from the flowable medium in one or more isolation regions of the microfluidic device; and freezing the microfluidic device including the one or more biological cells sequestered therein.

34 Claims, 12 Drawing Sheets

(56) References Cited

U.S. PATENT DOCUMENTS

| | | | |
|---|---|---|---|
| 2016/0171686 A1 | 6/2016 | Du | |
| 2016/0184821 A1 | 6/2016 | Hobbs | |
| 2016/0193604 A1 | 6/2016 | McFarland | |
| 2016/0252495 A1 | 9/2016 | Ricicova | |
| 2016/0312165 A1 | 10/2016 | Lowe | |
| 2017/0252744 A1* | 9/2017 | Baroud | B01L 3/502746 |

FOREIGN PATENT DOCUMENTS

| | | | |
|---|---|---|---|
| EP | 2316565 | | 5/2011 |
| EP | 2316565 A1 | | 5/2011 |
| EP | 2647434 | | 5/2017 |
| WO | WO 2007/085385 | * | 6/2007 |
| WO | 2007/120829 | | 10/2007 |
| WO | 2007120829 A2 | | 10/2007 |
| WO | WO 2007/120829 | | 10/2007 |
| WO | 2010/009365 | | 1/2010 |
| WO | 2010/056755 | | 5/2010 |
| WO | 2010056755 A2 | | 5/2010 |
| WO | WO 2010147078 | | 12/2010 |
| WO | 2012/162779 A1 | | 12/2012 |
| WO | WO 2013148745 | | 10/2013 |
| WO | 2014011985 A1 | | 1/2014 |
| WO | WO 2014070873 | | 5/2014 |
| WO | 2014/145075 | | 9/2014 |

OTHER PUBLICATIONS

PCT Invitation to Pay Additional Fees for International Application No. PCT/US2016/029032, Applicant Berkeley Lights, Inc., dated Jul. 4, 2016 (9 pages).
Hung et al., Continuous Perfusion Microfluidic Cell Culture Array for High-Throughput Cell-Based Assays, Biotech and Bioengineering 89(1): 1-8 (2004). Dec. 3, 2004.
Chiou et al., Massively parallel manipulation of single cells and microparticles using optical images, Nature 436:370-73, Jul. 21, 2005.
Yi, Microfluidics technology for manipulation and analysis of biological cells, Analytica Chimica Acta 560:1-23, Jan. 25, 2006.
Nevill et al., Integrated microfluidic cell culture and lysis on a chip, Lab on a Chip 7:1689-95 (Oct. 19, 2007).
Hsu et al., Sorting of Differentiated Neurons using Phototransistor-based Optoelectronic Tweezers for Cell Replacement Therapy of Neurodegenerative Diseases, IEEE Conference on Transducers (Jun. 21-25, 2009).
Valley et al., Optoelectronic Tweezers as a Tool for Parallel Single-Cell Manipulation and Stimulation, IEEE Transactions on Biomedical Circuits and Systems 3(6):424-30 (2009). Dec. 1, 2009.
Young et al., Fundamentals of microfluidic cell culture in controlled microenvironments, Chem Soc Rev 39(3):1036-48 (Mar. 2010).
Reichman, "Extended in vitro maturation of immature oocytes from stimulated cycles: an analysis of fertilization potential, embryo development, and reproductive outcomes", J. Assist. Reprod. Genet. vol. 27, 347-356, Jan. 20, 2010.
Swain et al., Advances in embryo culture platforms: novel approaches to improve preimplantation embryo development through modifications of the microenvironment, Human Reproduction Update 17(4):541-57 (Mar. 31, 2011).
Lowe et al, Deposition of Dense Siloxane Monolayers from Water and Trimethoxysilane Vapor, Langmuir 2011, 27, 9928-9935, Jul. 1, 2011.
Banuls et al. Chemical surface modifications for the development of silicon-based label-free integrated optical (IO) biosensors: A review. Jan. 23, 2013.
Somaweera et al., Generation of a Chemical Gradient Across an Array of 256 Cell Cultures in a Single Chip, Analyst., Oct. 7, 2013, vol. 138, No. 19, pp. 5566-5571.
Chung et al., Microwells support high-resolution time-lapse imaging and development of preimplanted mouse embryos, Biomicrofluidics 9:022407 (Apr. 28, 2015).
2nd Examination Report for AU Patent Appln. No. 2016252995 dated Oct. 28, 2020, 5 pages.
Foreign Office Action for JP Patent Application No. 2017-555231 dated Feb. 12, 2020, 6 pgs.

* cited by examiner

FREEZING AND ARCHIVING CELLS ON A MICROFLUIDIC DEVICE

RELATED APPLICATION DATA

The present application claims the benefit under 35 U.S.C. § 119 to U.S. provisional patent application Ser. No. 62/151,382, filed Apr. 22, 2015. The foregoing application is hereby incorporated by reference into the present application in its entirety.

FIELD

The present disclosure relates generally to the processing and storing of biological cells using microfluidic devices.

BACKGROUND

As the field of microfluidics continues to progress, microfluidic devices have become convenient platforms for processing and manipulating micro-objects, such as biological cells. Even so, the full potential of microfluidic devices, particularly as applied to the biological sciences, has yet to be realized. For example, while microfluidic devices have been applied to the analysis of biological cells, containers such as test tubes and microtiter plates continue to be used for storage and archiving of such cells. These types of containers (test tubes and microtiter plates) do not interface well with microfluidic devices. Moreover, they are relatively large and thus occupy large amounts of costly freezer space, and require a significant amount of costly cell preservation reagents, when they are used for the storage and archiving of biological cells.

SUMMARY

In accordance with the embodiments disclosed herein, an exemplary method for processing and storing biological cells in a microfluidic device includes (i) introducing a flowable medium into a microfluidic device, the flowable medium including biological cells, (ii) sequestering one or more biological cells from the flowable medium in one or more isolation regions of the microfluidic device, and (iii) freezing the microfluidic device including the one or more biological cells sequestered therein. The microfluidic device can include a flow region to which the one or more isolation regions are fluidically connected. While as few as a single biological cell may be initially sequestered within the microfluidic device, more typically, at least a single cell will be sequestered in each of a plurality of isolation regions within the microfluidic device. Furthermore, a typical microfluidic device used in embodiments of the method may have anywhere from dozens, to hundreds or more isolation regions, with each isolation region having a volume (without limitation) in a range of about $1.5 \times 10^5$ cubic microns to about $1.5 \times 10^6$ cubic microns, and thus be capable of sequestering as many as about 10 cells to about 50 cells. In one embodiment, prior to freezing the microfluidic device, one or more of the sequestered ("starting") cells in a first isolation region of the microfluidic device can be cultured to generate a plurality of "new" cells in the first isolation region adequate in number (e.g., at least 8, and more preferably at least 10, 16, 20, 24, 30 or more cells), so that at least one viable cell will be present in the first isolation region after thawing the microfluidic device.

Although it is not essential for practicing the disclosed methods, in preferred embodiments, prior to freezing the microfluidic device, an inventory of the contents of the microfluidic device is created and stored for future retrieval and reference. For example, the inventory may include, by way of example and without limitation, an identity (e.g., the origin of the sequestered cells, such as a patient/subject sample number) and isolation region location for each of the one or more sequestered cells. In some embodiments, the inventory further includes information identifying one or more of (i) how the biological cells in the flowable medium were obtained, (ii) processing, if any, performed on the biological cells prior to or after their introduction into the microfluidic device, (iii) processing, if any, performed on the one or more sequestered biological cells after their sequester within an isolation chamber; and (iv) data obtained in the course of any such pre- or post-sequestration processing. The microfluidic device may include identifying indicia, such as a barcode, sticker, RFID, or the like, and the device inventory may be stored in a database that references the identifying indicia for the device. Alternatively or additionally, the device inventory may be stored in a memory chip (e.g., an EEPROM or the like) coupled to, and frozen with, the microfluidic device.

In various embodiments, the method further includes (prior to freezing the device) introducing a cell preservation reagent, such as dimethyl sulfoxide (DMSO), into the microfluidic device. In one such embodiment, DMSO is introduced into the microfluidic device at a respective concentration and duration selected such that the one or more sequestered biological cells are substantially surrounded by a solution containing about 10% DMSO at the time of freezing the microfluidic device. In one such embodiment, DMSO is introduced into the microfluidic device at a concentration of about 15% to about 25% by volume (depending, e.g., on the ratio of the volume of the flow region to a total volume of the isolation regions in the microfluidic device), and allowed to diffuse into the one or more isolation regions containing sequestered biological cells. In another such embodiment, DMSO is perfused through the microfluidic device for an amount of time sufficient to achieve a DMSO concentration of about 10% in each of the one or more isolation regions.

In various embodiments, freezing the microfluidic device may include an initial controlled cooling of the microfluidic device to a temperature of near freezing (e.g., about 4° C., or freezing (e.g., about 0° C.), followed by additional cooling of the microfluidic device to a subzero temperature. By way of example, and without limitation, the initial controlled cooling of the microfluidic device may be at a rate in a range of about 1° C. per minute to about 2° C. per minute, although a slower rate (e.g., 0.1° C. per minute) or faster rate (e.g., 3° C. or more per minute) may also be used. In various embodiments, the subzero temperature is about −20° C. or less, and more preferably is about −80° C. or less, including in some embodiments about −150° C. or less.

The method may further include thawing the microfluidic device, for example, by one or both of (i) a controlled heating of the microfluidic device, and (ii) allowing the microfluidic device to self-heat to room temperature, in order to test, evaluate, assay, sequence and/or otherwise use the sequestered cells after thawing. For example, in some embodiments, after thawing the microfluidic device, the method includes culturing one or more viable cells in the microfluidic device (e.g., by continuous or intermittent perfusion of a flowable cell growth medium through the microfluidic device) to thereby generate additional cells therein. In such embodiments, the method may further include (after thawing) identifying which of the one or more sequestered cells and/or cells generated therefrom are viable after thawing the microfluidic device, and/or retrieving from the microfluidic device at least one sequestered cell and/or cells generated therefrom. By way of example, after thawing, an assay may be performed of one or more cells in the microfluidic device to detect a cell secretion (e.g., an immunological molecule comprising an antibody or a cytokine) or a cell surface marker.

In certain embodiments, the methods may be performed on a microfluidic device having one or more of its inner surfaces (e.g., a substrate surface, a cover surface, and/or the surfaces of the circuit material) conditioned so as to reduce fouling and/or cell sticking. For example, the flow region and the one or more isolation regions can be treated with a blocking solution to prevent fouling and/or reduce cell adhesion. Thus, the blocking solution can comprise a blocking agent that binds to the one or more inner surfaces, such as serum, serum albumin (e.g., BSA), polymer, detergent, enzymes, or any combination thereof.

In certain embodiments, the microfluidic device can comprise an inner substrate surface (and/or an inner cover surface and/or inner surfaces of the circuit material) that comprise a coating material. In some embodiments, the coating material includes molecules having a linking group and an alkyl moiety. The linking group can be covalently bonded to the inner substrate surface, and can be, for example, a siloxy linking group. The alkyl moiety can be, for example, an unsubstituted alkyl moiety or a substituted alkyl moiety, such as a fluoroalkyl moiety or a perfluoroalkyl moiety. The alkyl moiety can include a linear chain of carbons comprising at least 10 carbon atoms (e.g., at least 12, 14, 16, 18, 20, 22, or more carbon atoms). The molecules of the coating material can form a densely-packed monolayer structure covalently bound to the inner substrate surface (and/or the inner cover surface and/or the inner surfaces of the circuit material).

In some embodiments, the coating material comprises molecules having a linking group and a cationic moiety and/or an anionic moiety, wherein the linking group is covalently bonded to the inner substrate surface (and/or the inner cover surface and/or the inner surfaces of the circuit material). The cationic moiety can include a quaternary ammonium group. The anionic moiety can include a phosphonic acid, carboxylic acid, or sulfonic acid. In some related embodiments, the coating material can comprise molecules having a linking group and a zwitterionic moiety, wherein the linking group is covalently bound to the inner substrate surface (and/or the inner cover surface and/or the inner surfaces of the circuit material). The zwitterionic moiety is selected from carboxybetaines, sulfobetaines, sulfamic acids, and amino acids. In some embodiments, the cationic, anionic, or zwitterionic moieties are capable of ionically bonding with a blocking agent).

In some embodiments, the coating material comprises a polymer comprising alkylene ether moieties, saccharide moieties, or amino acid moieties. For example, the coating material can comprise dextran. Alternatively, or in addition, the coating material can comprise poly-ethylene glycol.

Other and further aspects and features of embodiments of the disclosed inventions will become apparent from the ensuing detailed description in view of the accompanying figures.

DETAILED DESCRIPTION

Figure 1A:
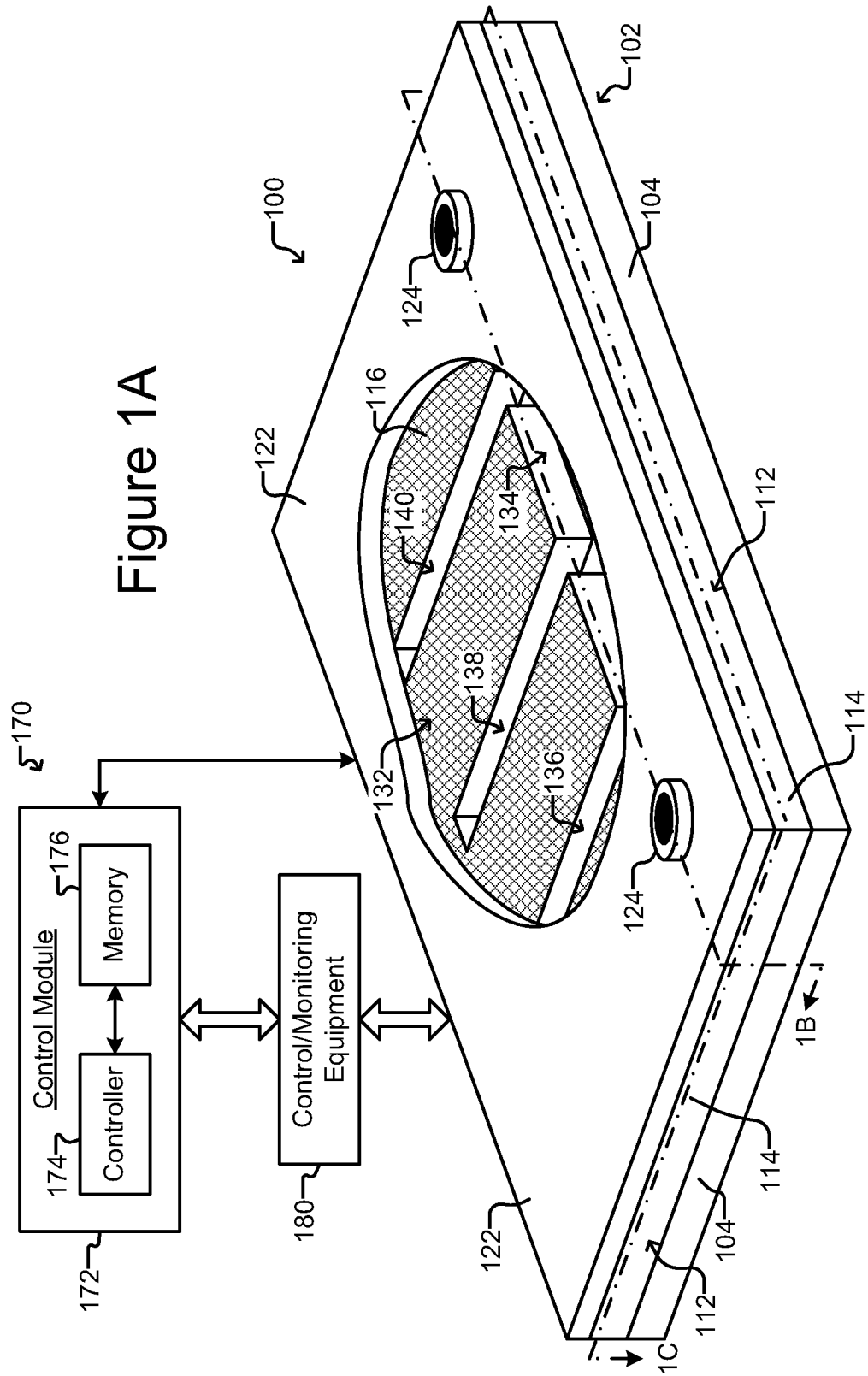
FIG. 1A is a perspective view of an exemplary embodiment of a system including a microfluidic device for culturing biological cells.

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent. The term "ones" means more than one.

As used herein, the term "micro-object" can encompass one or more of the following: inanimate micro-objects such as microparticles, microbeads (e.g., polystyrene beads, Luminex™ beads, or the like), magnetic beads, paramagnetic beads, microrods, microwires, quantum dots, and the like; biological micro-objects such as cells (e.g., embryos, oocytes, sperms, cells dissociated from a tissue, blood cells, immunological cells, including T cells, B cells, macrophages, NK cells, dendritic cells (DCs), and the like, hybridomas, cultured cells, cells dissociated from a tissue, cells from a cell line, such as CHO cells, which may be transfected and/or transformed, cancer cells, including circulating tumor cells (CTCs), infected cells, reporter cells, and the like), liposomes (e.g., synthetic or derived from membrane preparations), lipid nanorafts, and the like; or a combination of inanimate micro-objects and biological micro-objects (e.g., microbeads attached to cells, liposome-coated micro-beads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231. Beads may further have other moieties/molecules covalently or non-covalently attached, such as fluorescent labels, proteins, small molecule signaling moieties, antigens, or chemical/biological species capable of use in an assay.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

In some embodiments, a microfluidic device can comprise "swept" regions and "unswept" regions. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 300 times the length, at least 400 times the length, at least 500 times the length, or longer. In some embodiments, the length of a flow channel is in the range of from about 20,000 microns to about 100,000 microns, including any range therebetween. In some embodiments, the horizontal dimension is in the range of from about 100 microns to about 300 microns (e.g., about 200 microns) and the vertical dimension is in the range of from about 25 microns to about 100 microns, e.g., from about 40 to about 50 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

In certain embodiments, a flow channel of a micro-fluidic device is an example of a swept region (defined above) while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. For example, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

System Including a Microfluidic Device.

Figure 1B:
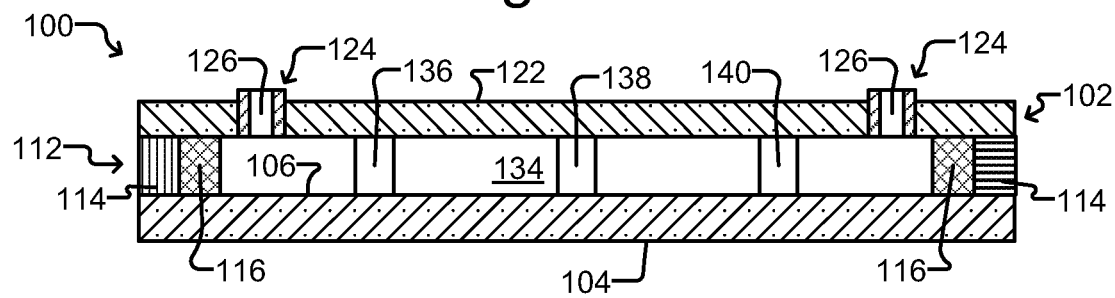
FIG. 1B is a side, cross-sectional view of the microfluidic device of FIG. 1A.
Figure 1C:
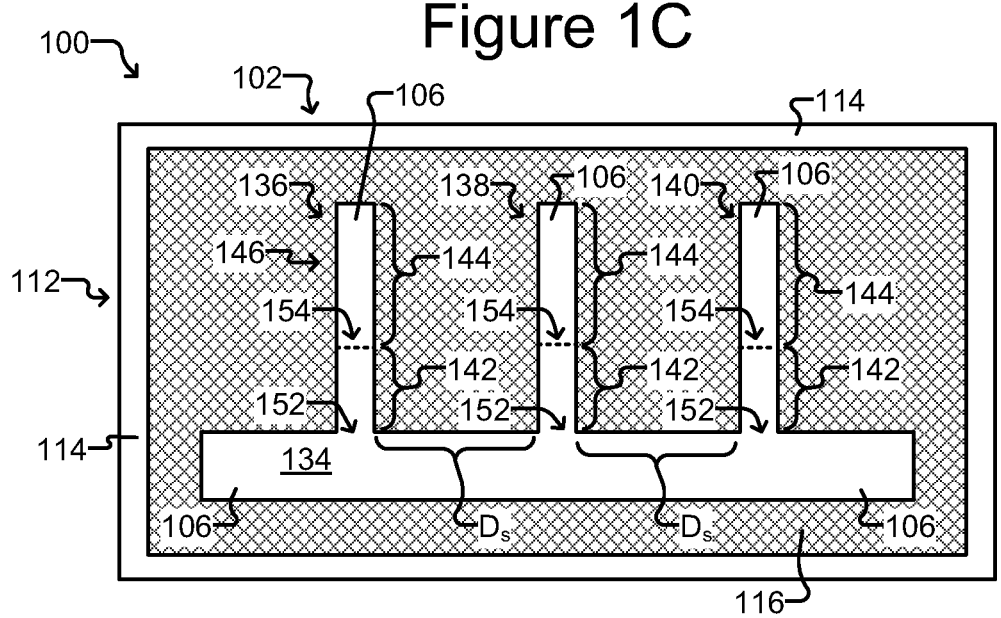
FIG. 1C is a top, cross-sectional view of the microfluidic device of FIG. 1A.

FIGS. 1A-1C illustrate an example of a system having a microfluidic device 100 which may be used in the methods described herein. As shown, the microfluidic device 100 encloses a microfluidic circuit 132 comprising a plurality of interconnected fluidic circuit elements. In the example illustrated in FIGS. 1A-1C, the microfluidic circuit 132 includes a flow channel 134 to which isolation chambers 136, 138, 140 are fluidically connected. Although one flow channel 134 and three isolation chambers 136, 138, 140 are shown in the illustrated embodiment, it should be understood that there may be more than one flow channel 134, and more or fewer than three isolation chambers 136, 138, 140, respectively, in alternate embodiments. The microfluidic circuit 132 can also include additional or different fluidic circuit elements such as fluidic chambers, reservoirs, and the like.

The microfluidic device 100 comprises an enclosure 102 enclosing the microfluidic circuit 132, which can contain one or more fluidic media. Although the device 100 can be physically structured in different ways, in the embodiment shown in FIGS. 1A-1C, the enclosure 102 includes a support structure 104 (e.g., a base), a microfluidic circuit structure 112, and a cover 122. The support structure 104, microfluidic circuit structure 112, and the cover 122 can be attached to each other. For example, the microfluidic circuit structure 112 can be disposed on the support structure 104, and the cover 122 can be disposed over the microfluidic circuit structure 112. With the support structure 104 and the cover 122, the microfluidic circuit structure 112 can define the microfluidic circuit 132. An inner surface of the microfluidic circuit 132 is identified in the figures as 106.

The support structure 104 can be at the bottom and the cover 122 at the top of the device 100 as illustrated in FIGS. 1A and 1B. Alternatively, the support structure 104 and cover 122 can be in other orientations. For example, the support structure 104 can be at the top and the cover 122 at the bottom of the device 100. Regardless of the configuration, one or more fluid access (i.e., ingress and egress) ports 124 are provided, each fluid access port 124 comprising a passage 126 in communication with the microfluidic circuit 132, which allow for a fluid material to be flowed into, or out of, the enclosure 102. The fluid passages 126 may include a valve, a gate, a pass-through hole, or the like. Although two fluid access ports 124 are shown in the illustrated embodiment, it should be understood that alternate embodiments of the device 100 can have only one or more than two fluid access ports 124 providing ingress and egress of fluid material into and out of the microfluidic circuit 132.

The microfluidic circuit structure 112 can define or otherwise accommodate circuit elements of the microfluidic circuit 132, or other types of circuits located within the enclosure 102. In the embodiment illustrated in FIGS. 1A-1C, the microfluidic circuit structure 112 comprises a frame 114 and a microfluidic circuit material 116.

The support structure 104 can comprise a substrate or a plurality of interconnected substrates. For example, the support structure 104 can comprise one or more interconnected semiconductor substrates, printed circuit boards (PCB), or the like, and combinations thereof (e.g. a semiconductor substrate mounted on a PCB). The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define microfluidic circuit elements and interconnections of the microfluidic circuit 132. The microfluidic circuit material 116 can comprise a flexible material (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicon (e.g. photo-patternable silicon), photo-resist (e.g., SU8), or the like. In some embodiments, such materials—and thus the microfluidic circuit material 116—can be rigid and/or substantially impermeable to gas. Regardless of the material(s) used, the microfluidic circuit material 116 is disposed on the support structure 104, within the frame 114.

Figure 2:
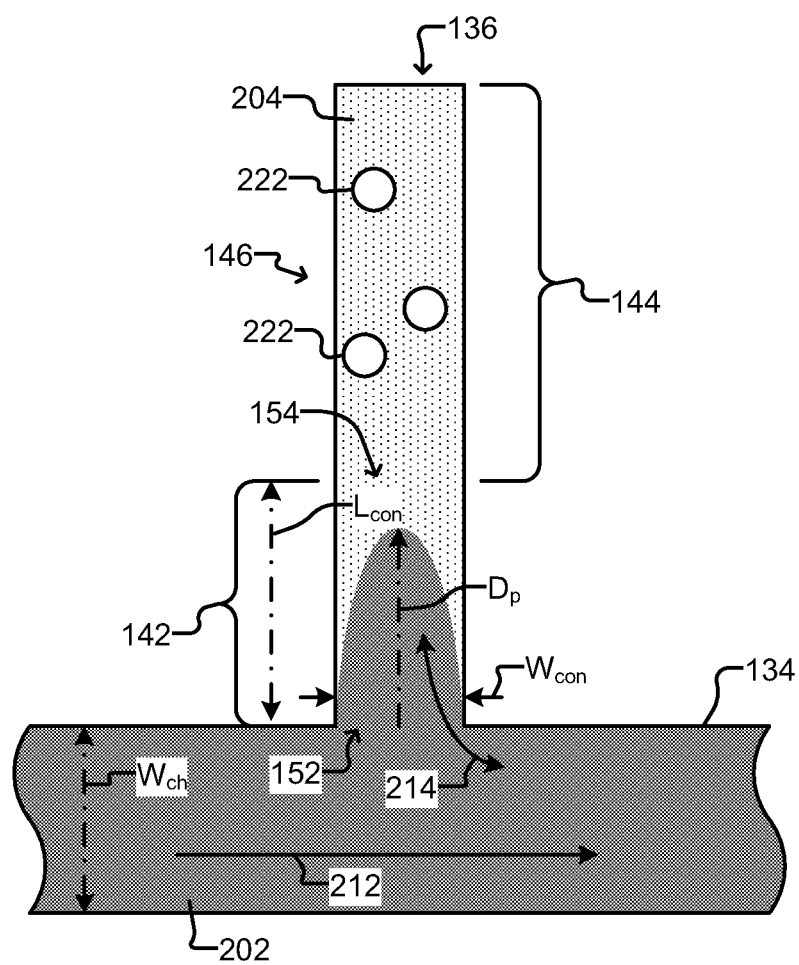
FIG. 2 illustrates an example of an isolation chamber that may be used in the microfluidic device of FIG. 1A, in which a length of a connection region from a flow channel to an isolation region is greater than a penetration depth of medium flowing in the flow channel.
Figure 3:
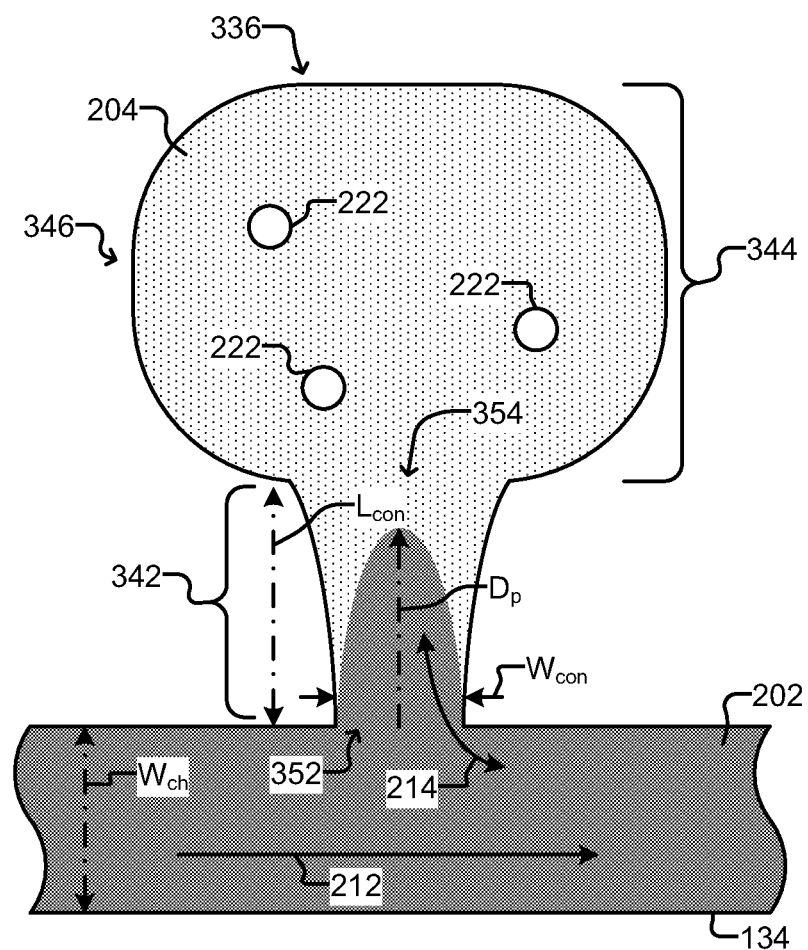
FIG. 3 is another example of an isolation chamber that may be used in the microfluidic device of FIG. 1A, including a connection region from a flow channel to an isolation region that is longer than a penetration depth of medium flowing in the flow channel.

The cover 122 can be an integral part of the frame 114 and/or the microfluidic circuit material 116. Alternatively, the cover 122 can be a structurally distinct element (as illustrated in FIGS. 1A and 1B). The cover 122 can comprise the same or different materials than the frame 114 and/or the microfluidic circuit material 116. Similarly, the support structure 104 can be a separate structure from the frame 114 or microfluidic circuit material 116, as illustrated, or an integral part of the frame 114 or microfluidic circuit material 116. Likewise the frame 114 and microfluidic circuit material 116 can be separate structures as shown in FIGS. 1A-1C or integral portions of the same structure. In some embodiments, the cover or lid 122 is made from a rigid material. The rigid materials may be glass or the like. In some embodiments, the rigid material may be conductive (e.g. ITO-coated glass) and/or modified to support cell adhesion, viability and/or growth. The modification may include a coating of a synthetic or natural polymer. In some embodiments, a portion of the cover or lid 122 that is positioned over a respective isolation chamber 136, 138, 140 of FIGS. 1A-1C, or the equivalent in the below-described embodiments illustrated in FIGS. 2, 3, and 4, is made of a deformable material, including but not limited to PDMS. Thus the cover or lid 122 may be a composite structure having both rigid and deformable portions. In some embodiments, the cover 122 and/or the support structure 104 is transparent to light.

The cover 122 may also include at least one material that is gas permeable, including but not limited to PDMS.

Other System Components.

FIG. 1A also illustrates simplified block diagram depictions of a control/monitoring system 170 that can be utilized in conjunction with the microfluidic device 100, which together provide a system for biological cell culturing. As shown (schematically), the control/monitoring system 170 includes a control module 172 and control/monitoring equipment 180. The control module 172 can be configured to control and monitor the device 100 directly and/or through the control/monitoring equipment 180.

The control module 172 includes a controller 174 and a memory 176. The controller 174 can be, for example, a digital processor, computer, or the like, and the memory 176 can be, for example, a non-transitory digital memory for storing data and machine executable instructions (e.g., software, firmware, microcode, or the like) as non-transitory data or signals. The controller 174 can be configured to operate in accordance with such machine executable instructions stored in the memory 176. Alternatively or in addition, the controller 174 can comprise hardwired digital circuitry and/or analog circuitry. The control module 172 can thus be configured to perform (either automatically or based on user-directed input) any process useful in the methods described herein, step of such a process, function, act, or the like discussed herein.

The control/monitoring equipment 180 can comprise any of a number of different types of devices for controlling or monitoring the microfluidic device 100 and processes performed with the microfluidic device 100. For example, the control/monitoring equipment 180 can include power sources (not shown) for providing power to the microfluidic device 100; fluidic media sources (not shown) for providing fluidic media to or removing media from the microfluidic device 100; motive modules such as, by way of non-limiting example, a selector control module (described below) for controlling selection and movement of micro-objects (not shown) in the microfluidic circuit 132; image capture mechanisms such as, by way of non-limiting example, a detector (described below) for capturing images (e.g., of micro-objects) inside the microfluidic circuit 132; stimulation mechanisms such as, by way of non-limiting example, the below-described light source 320 of the embodiment illustrated in FIG. 1D, for directing energy into the microfluidic circuit 132 to stimulate reactions; and the like.

Figure 1D:
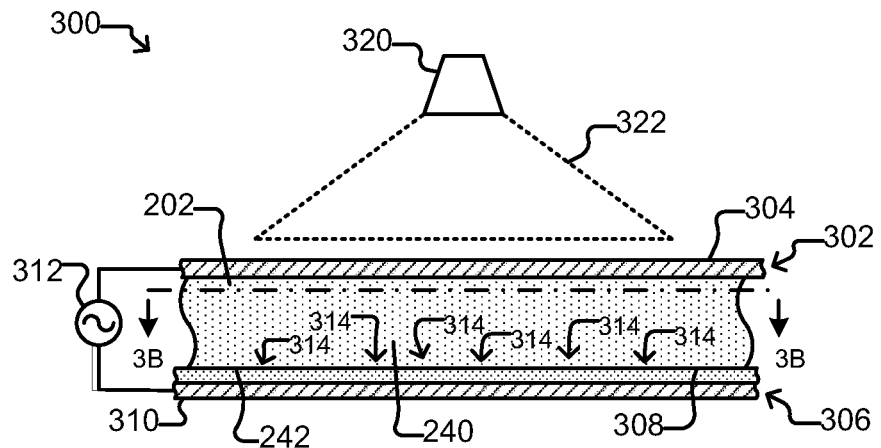
FIG. 1D is side cross-sectional view of an embodiment of a microfluidic device having a dielectrophoresis (DEP) configuration.
Figure 1E:
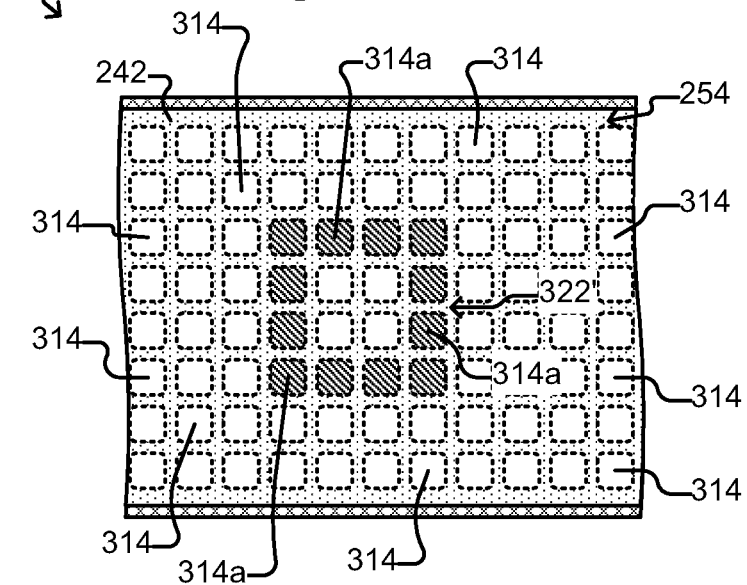
FIG. 1E is a top, cross-sectional view of one embodiment of the microfluidic device of FIG. 1D.
Figure 4A:
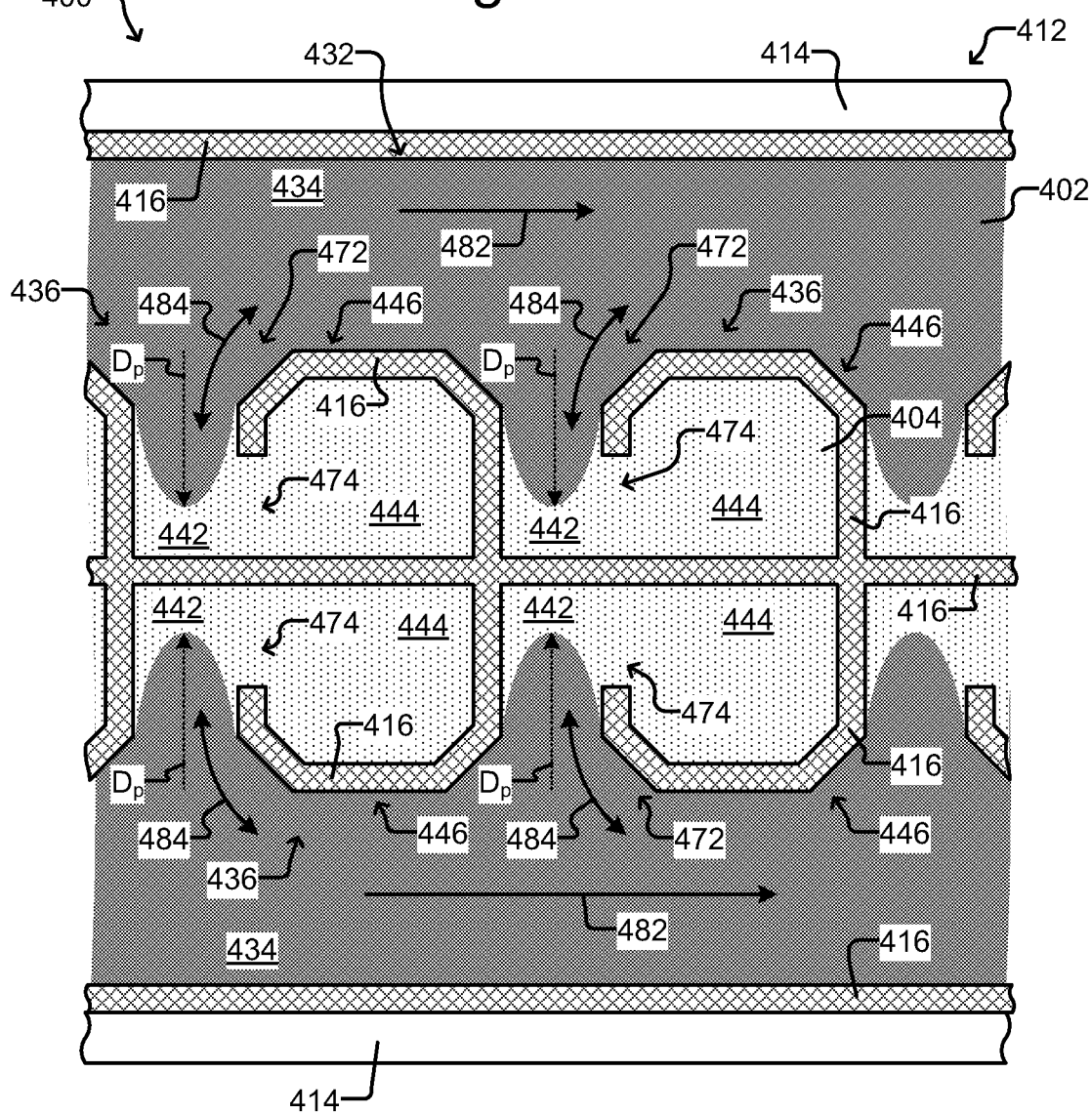
FIGS. 4A-C show another embodiment of a microfluidic device, including a further example of an isolation chamber used therein.
Figure 4B:
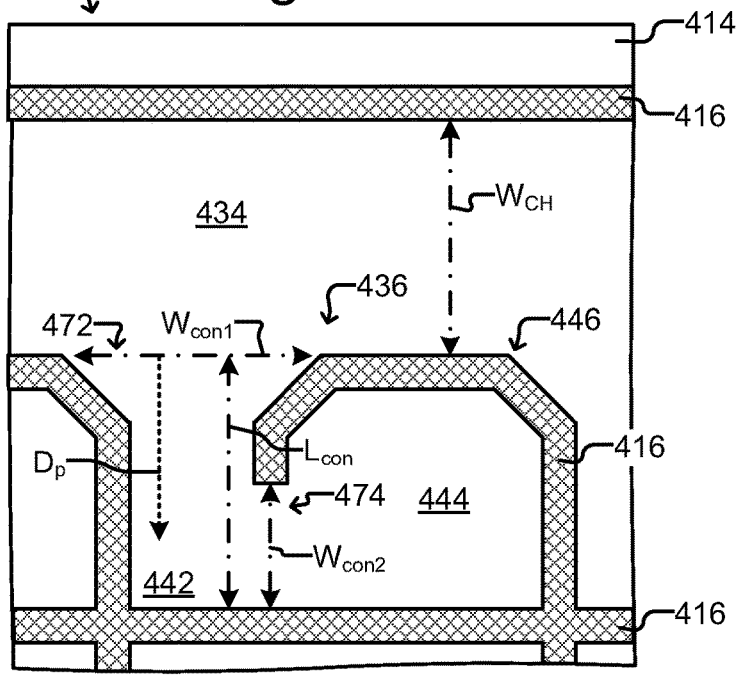
Figure 4C:
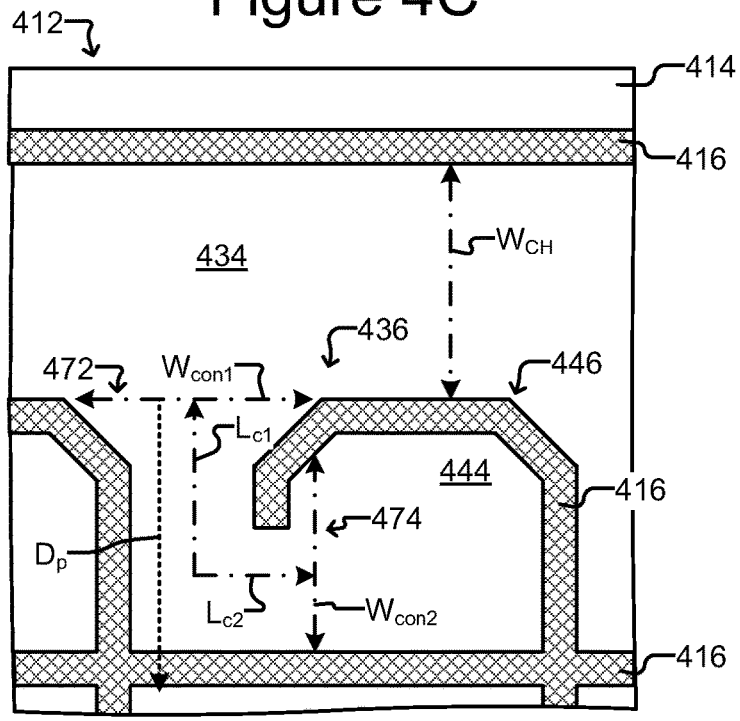

More particularly, an image capture detector can include one or more image capture devices and/or mechanisms for detecting events in the flow regions, including but not limited to flow channel 134 of the embodiments shown in FIGS. 1A-1C, 2, and 3, flow channel 434 of the embodiment shown in FIGS. 4A-4C, and flow region 240 of the embodiment shown in FIG. 1D-1E, and/or the isolation chambers of the respective illustrated microfluidic devices 100, 300, and 400, including micro-objects contained in a fluidic medium occupying the respective flow regions and/or isolation chambers. For example, the detector can comprise a photodetector capable of detecting one or more radiation characteristics (e.g., due to fluorescence or luminescence) of a micro-object (not shown) in the fluidic medium. Such a detector can be configured to detect, for example, that one or more micro-objects (not shown) in the medium are radiating electromagnetic radiation and/or the approximate wavelength, brightness, intensity, or the like of the radiation. The detector may capture images under visible, infrared, or ultraviolet wavelengths of light. Examples of suitable photodetectors include without limitation photomultiplier tube detectors and avalanche photodetectors.

Examples of suitable imaging devices that the detector can comprise include digital cameras or photosensors such as charge coupled devices and complementary metal-oxide-semiconductor (CMOS) imagers. Images can be captured with such devices and analyzed (e.g., by the control module 172 and/or a human operator).

A flow controller can be configured to control a flow of the fluidic medium in the flow regions/flow channels/swept regions of the respective illustrated microfluidic devices 100, 300, and 400. For example, the flow controller can control the direction and/or velocity of the flow. Non-limiting examples of such flow control elements of the flow controller include pumps and fluid actuators. In some embodiments, the flow controller can include additional elements such as one or more sensors for sensing, for example, the velocity of the flow and/or the pH of the medium in the flow region/flow channel/swept region.

The control module 172 can be configured to receive signals from and control the selector control module, the detector, and/or the flow controller.

Referring in particular to the embodiment shown in FIG. 1D, a light source 320 may direct light useful for illumination and/or fluorescent excitation into the microfluidic circuit 132. Alternatively, or in addition, the light source may direct energy into the microfluidic circuit 132 to stimulate reactions which include providing activation energy needed for DEP configured microfluidic devices to select and move micro-objects. The light source may be any suitable light source capable of projecting light energy into the microfluidic circuit 132, such as a high pressure Mercury lamp, Xenon arc lamp, diode, laser or the like. The diode may be an LED. In one non-limiting example the LED may be a broad spectrum "white" light LED (e.g. a UHP-T-LED-White by Prizmatix). The light source may include a projector or other device for generating structured light, such as a digital micromirror device (DMD), a MSA (microarray system) or a laser.

Motive Modules for Selecting and Moving Micro-Objects Including Biological Cells.

As described above, the control/monitoring equipment 180 can comprise motive modules for selecting and moving micro-objects (not shown) in the microfluidic circuit 132. A variety of motive mechanisms can be utilized. For example, dielectrophoresis (DEP) mechanisms can be utilized to select and move micro-objects (not shown) in the microfluidic circuit. The support structure 104 and/or cover 122 of the microfluidic device 100 of FIGS. 1A-1C can comprise DEP configurations for selectively inducing DEP forces on micro-objects (not shown) in a fluidic medium (not shown) in the microfluidic circuit 132 and thereby select, capture, and/or move individual micro-objects. The control/monitoring equipment 180 can include one or more control modules for such DEP configurations. Micro-objects, including cells, may alternatively be moved within the microfluidic circuit or exported from the microfluidic circuit using gravity, magnetic force, fluid flow and/or the like.

One example of a microfluidic device having a DEP configuration that comprises support structure 104 and cover 122 is the microfluidic device 300 illustrated in FIGS. 1D and 1E. While for purposes of simplicity FIGS. 1D and 1E show a side cross-sectional view and a top cross-sectional view of a portion of a flow region 240 of the microfluidic device 300, it should be understood that the microfluidic device 300 may also include one or more isolation chambers, as well as one or more additional flow regions/flow channels, such as those described herein with respect to microfluidic devices 100 and 400, and that a DEP configuration may be incorporated in any of such regions of the microfluidic device 300. It should be further appreciated that any of the above or below described microfluidic system components may be incorporated in and/or used in combination with microfluidic device 300. For example, a control module 172 including control/monitoring equipment 180 described above in conjunction with microfluidic device 100 of FIGS. 1A-1C may also be used with the microfluidic device 300, including one or more of an image-capture detector, flow controller, and selector control module.

As seen in FIG. 1D, the microfluidic device 300 includes a first electrode 304, a second electrode 310 spaced apart from the first electrode 304, and an electrode activation substrate 308 overlying electrode 310. The respective first electrode 304 and electrode activation substrate 308 define opposing surfaces of the flow region 240, wherein a medium 202 contained in the flow region 240 provides a resistive flow path between electrode 304 and the electrode activation substrate 308. A power source 312 configured to be connected to the first electrode 304 and the second electrode 310 and create a biasing voltage between the electrodes, as required for the generation of DEP forces in the flow region 240, is also shown. The power source 312 can be, for example, an alternating current (AC) power source.

In certain embodiments, the microfluidic device 300 illustrated in FIGS. 1D and 1E can have an optically-actuated DEP configuration, such as an Opto-Electronic Tweezer (OET) configuration. In such embodiments, changing patterns of light 322 from the light source 320, which may be controlled by the selector control module, can be used to selectively activate changing patterns of "DEP electrodes" on targeted locations 314 on the inner surface 242 of the flow region 240. Hereinafter the targeted regions 314 on the inner surface 242 of the flow region 240 are referred to as "DEP electrode regions."

In the example illustrated in FIG. 1E, a light pattern 322' directed onto the inner surface 242 illuminates the cross-hatched DEP electrode regions 314a in the square pattern shown. The other DEP electrode regions 314 are not illuminated and are hereinafter referred to as "dark" DEP electrode regions 314. The electrical impedance through the DEP electrode activation substrate 308 (i.e., from each dark electrode region 314 on the inner surface 242 to the second electrode 310) is greater than the electrical impedance through the medium 202 (i.e., from the first electrode 304, across the medium 202 in the flow region 240, to the dark DEP electrode regions 314 on the inner surface 242). Illuminating the DEP electrode regions 314a, however, reduces the impedance through the electrode activation substrate 308 (i.e., from the illuminated DEP electrode regions 314a on the inner surface 242 to the second electrode 310) to less than the impedance through the medium 202 (i.e., from the first electrode 304, across the medium 202 in the flow region 240, to the illuminated DEP electrode regions 314a on the inner surface 242).

With the power source 312 activated, the foregoing creates an electric field gradient in the medium 202 between the respective illuminated DEP electrode regions 314a and adjacent dark DEP electrode regions 314, which in turn creates localized DEP forces that attract or repel nearby micro-objects (not shown) in the fluid medium 202. In this manner, DEP electrodes that attract or repel micro-objects in the medium 202 can be selectively activated and deactivated in order to manipulate, i.e., move, the micro-objects within the flow region 240 by changing the light patterns 322 projected from the light source 320 into the microfluidic device 300. The light source 320 can be, for example, a laser or other type of structured light source, such as a projector. Whether the DEP forces attract or repel nearby micro-objects can depend on parameters such as, without limitation, the frequency of the power source 312 and the dielectric properties of the medium 202 and/or micro-objects (not shown).

The square pattern 322' of illuminated DEP electrode regions 314a illustrated in FIG. 1E is an example only. Any number of patterns or configurations of DEP electrode regions 314 can be selectively illuminated by a corresponding pattern of light 322 projected from the source 320 into the device 300, and the pattern of illuminated DEP electrode regions 322' can be repeatedly changed by changing the light pattern 322 in order to manipulate micro-objects in the fluid medium 202.

In some embodiments, the electrode activation substrate 308 can be a photoconductive material, and the rest of the inner surface 242 can be featureless. For example, the photoconductive material can be made from amorphous silicon, and can form a layer having a thickness of about 500 nm to about 2 μm in thickness (e.g. substantially 1 micron in thickness). In such embodiments, the DEP electrode regions 314 can be created anywhere and in any pattern on the inner surface 242 of the flow region 240 in accordance with the light pattern 322 (e.g., light pattern 322' shown in FIG. 1E). The number and pattern of the illuminated DEP electrode regions 314a are thus not fixed, but correspond to the respective projected light patterns 322. Examples are illustrated in U.S. Pat. No. 7,612,355, in which un-doped amorphous silicon material is used as an example of photoconductive material that can compose the electrode activation substrate 308.

In other embodiments, the electrode activation substrate 308 can comprise a substrate comprising a plurality of doped layers, electrically insulating layers, and electrically conductive layers that form semiconductor integrated circuits such as is known in semiconductor fields. For example, the electrode activation substrate 308 can comprise an array of photo-transistors. In such embodiments, electric circuit elements can form electrical connections between the DEP electrode regions 314 at the inner surface 242 of the flow region 240 and the second electrode 310 that can be selectively activated by the respective light patterns 322. When not activated, the electrical impedance through each electrical connection (i.e., from a corresponding DEP electrode region 314 on the inner surface 242, through the electrical connection, to the second electrode 310) can be greater than the impedance through the medium 202 (i.e., from the first electrode 304, through the medium 202, to the corresponding DEP electrode region 314 on the inner surface 242). When activated by light in the light pattern 322, however, the electrical impedance though the illuminated electrical connections (i.e., from each illuminated DEP electrode region 314a, through the electrical connection, to the second electrode 310) can be reduced to an amount less than the electrical impedance through the medium 202 (i.e., from the first electrode 304, through the medium 202, to the corresponding illuminated DEP electrode region 314a), thereby activating a DEP electrode at the corresponding DEP electrode region 314 as discussed above. DEP electrodes that attract or repel micro-objects (not shown) in the medium 202 can thus be selectively activated and deactivated at many different DEP electrode regions 314 at the inner surface 242 of the flow region 240 by the light pattern 322. Non-limiting examples of such configurations of the electrode activation substrate 308 include the phototransistor-based device 300 illustrated in FIGS. 21 and 22 of U.S. Pat. No. 7,956,339.

In other embodiments, the electrode activation substrate 308 can comprise a substrate comprising a plurality of electrodes, which may be either photo-actuated. Non-limiting examples of such configurations of the electrode activation substrate 308 include the photo-actuated devices 200, 400, 500, and 600 illustrated and described in U.S. Patent Application Publication No. 2014/0124370. In still other embodiments, a DEP configuration of the support structure 104 and/or cover 122 does not rely upon light activation of DEP electrodes at the inner surface of the microfluidic device, but uses selectively addressable and energizable electrodes positioned opposite to a surface including at least one electrode, such as described in U.S. Pat. No. 6,942,776.

In some embodiments of a DEP configured device, the first electrode 304 can be part of a first wall 302 (or cover) of the housing 102, and the electrode activation substrate 308 and second electrode 310 can be part of a second wall 306 (or base) of the housing 102, generally as illustrated in FIG. 1D. As shown, the flow region 240 can be between the first wall 302 and the second wall 306. The foregoing, however, is but an example. In alternative embodiments, the first electrode 304 can be part of the second wall 306 and one or both of the electrode activation substrate 308 and/or the second electrode 310 can be part of the first wall 302. Moreover, the light source 320 can alternatively be located underneath the housing 102. In certain embodiments, the first electrode 304 may be an indium-tin-oxide (ITO) electrode, though other materials may also be used.

When used with the optically-actuated DEP configurations of microfluidic device 300 of FIGS. 1D-1E, a selector control module can thus select a micro-object (not shown) in the medium 202 in the flow region 240 by projecting one or more consecutive light patterns 322 into the device 300 to activate a corresponding one or more DEP electrodes at DEP electrode regions 314 of the inner surface 242 of the flow region 240 in successive patterns that surround and "capture" the micro-object. The selector control module can then move the captured micro-object within the flow region 240 by moving the light pattern 322 relative to the device 300 (or the device 300 (and thus the captured micro-object therein) can be moved relative to the light source 320 and/or light pattern 322). For embodiments featuring electrically-actuated DEP configurations of microfluidic device 300, the selector control module can select a micro-object (not shown) in the medium 202 in the flow region 240 by electrically activating a subset of DEP electrodes at DEP electrode regions 314 of the inner surface 242 of the flow region 240 that form a pattern that surrounds and "captures" the micro-object. The selector control module can then move the captured micro-object within the flow region 240 by changing the subset of DEP electrodes that are being electrically activated.

Isolation Chamber Configurations.

Non-limiting examples of isolation chambers 136, 138, and 140 of device 100 are shown in FIGS. 1A-1C. With specific reference to FIG. 1C, each isolation chamber 136, 138, 140 comprises an isolation structure 146 defining an isolation region 144 and a connection region 142 that fluidically connects the isolation region 144 to the flow channel 134. The connection regions 142 each have a proximal opening 152 into the flow channel 134, and a distal opening 154 into the respective isolation region 144. The connection regions 142 are preferably configured so that a maximum penetration depth of a flow of a fluidic medium (not shown) flowing at a maximum velocity ($V_{max}$) in the flow channel 134 does not inadvertently extend into the isolation region 144. A micro-object (not shown) or other material (not shown) disposed in an isolation region 144 of a respective isolation chamber 136, 138, 140 can thus be isolated from, and not substantially affected by, a flow of medium (not shown) in the flow channel 134. The flow channel 134 can thus be an example of a swept region, and the isolation regions of the isolation chambers 136, 138, 140 can be examples of unswept regions. As noted above, the respective flow channel 134 and isolation chambers 136, 138, 140 are configured to contain one or more fluidic media (not shown). In the embodiment shown in FIGS. 1A-1C, the fluid access ports 124 are fluidly connected to the flow channel 134 and allow a fluidic medium (not shown) to be introduced into or removed from the microfluidic circuit 132. Once the microfluidic circuit 132 contains a fluidic medium, flows of specific fluidic media therein can be selectively generated in the flow channel 134. For example, a flow of a medium can be created from one fluid access port 124 functioning as an inlet to another fluid access port 124 functioning as an outlet.

FIG. 2 illustrates a detailed view of an example of an isolation chamber 136 of the device 100 of FIGS. 1A-1C. Isolation chambers 138, 140 can be configured similarly. Examples of micro-objects 222 located in isolation chamber 136 are also shown.

As is known, a flow of fluidic medium 202 (indicated by directional arrow 212) in the microfluidic flow channel 134 past a proximal opening 152 of the isolation chamber 136 can cause a secondary flow of the medium 202 (indicated by directional arrow 214) into and/or out of the isolation chamber 136. To isolate the micro-objects 222 in the isolation region 144 of the isolation chamber 136 from the secondary flow 214, the length $L_{con}$ of the connection region 142 from the proximal opening 152 to the distal opening 154 is preferably greater than a maximum penetration depth $D_p$ of the secondary flow 214 into the connection region 142 when the velocity of the flow 212 in the flow channel 134 is at a maximum ($V_{max}$). As long as the flow 212 in the flow channel 134 does not exceed the maximum velocity $V_{max}$, the flow 212 and resulting secondary flow 214 are limited to the respective flow channel 134 and connection region 142, and kept out of the isolation region 144 of the isolation chamber 136. The flow 212 in the flow channel 134 will thus not draw micro-objects 222 out of the isolation region 144 of isolation chamber 136.

Moreover, the flow 212 will not move miscellaneous particles (e.g., microparticles and/or nanoparticles) that may be located in the flow channel 134 into the isolation region 144 of the isolation chamber 136. Having the length $L_{con}$ of the connection region 142 be greater than the maximum penetration depth $D_p$ can thus prevent contamination of the isolation chamber 136 with miscellaneous particles from the flow channel 134 or from another isolation chamber 138, 140.

Because the flow channel 134 and the connection regions 142 of the isolation chambers 136, 138, 140 can be affected by the flow 212 of medium 202 in the flow channel 134, the flow channel 134 and connection regions 142 can be deemed swept (or flow) regions of the microfluidic circuit 132. The isolation regions 144 of the isolation chambers 136, 138, 140, on the other hand, can be deemed unswept (or non-flow) regions. For example, components (not shown) in a first medium 202 in the flow channel 134 can mix with a second medium 204 in the isolation region 144 substantially only by diffusion of the components of the first medium 202 from the flow channel 134 through the connection region 142 and into the second medium 204 in the isolation region 144. Similarly, components of the second medium 204 (not shown) in the isolation region 144 can mix with the first medium 202 in the flow channel 134 substantially only by diffusion of the components of the second medium 204 from the isolation region 144 through the connection region 142 and into the first medium 202 in the flow channel 134. It should be appreciated that the first medium 202 can be the same medium or a different medium than the second medium 204. Moreover, the first medium 202 and the second medium 204 can start out being the same, then become different, e.g., through conditioning of the second medium by one or more cells in the isolation region 144, or by changing the medium flowing through the flow channel 134.

The maximum penetration depth $D_p$ of the secondary flow 214 caused by the flow 212 in the flow channel 134 can depend on a number of parameters. Examples of such parameters include (without limitation) the shape of the flow channel 134 (e.g., the channel can direct medium into the connection region 142, divert medium away from the connection region 142, or simply flow past the connection region 142); a width $W_{ch}$ (or cross-sectional area) of the flow channel 134 at the proximal opening 152; a width $W_{con}$ (or cross-sectional area) of the connection region 142 at the proximal opening 152; the maximum velocity $V_{max}$ of the flow 212 in the flow channel 134; the viscosity of the first medium 202 and/or the second medium 204, and the like.

In some embodiments, the dimensions of the flow channel 134 and/or isolation chambers 136, 138, 140 are oriented as follows with respect to the flow 212 in the flow channel 134: the flow channel width $W_{ch}$ (or cross-sectional area of the flow channel 134) can be substantially perpendicular to the flow 212; the width $W_{con}$ (or cross-sectional area) of the connection region 142 at the proximal opening 152 can be substantially parallel to the flow 212; and the length $L_{con}$ of the connection region can be substantially perpendicular to the flow 212. The foregoing are examples only, and the dimensions of the flow channel 134 and isolation chambers 136, 138, 140 can be in additional and/or further orientations with respect to each other.

As illustrated in FIG. 2, the width $W_{con}$ of the connection region 142 can be uniform from the proximal opening 152 to the distal opening 154. The width $W_{con}$ of the connection region 142 at the distal opening 154 can thus be in any of the below-identified ranges of corresponding to the width $W_{con}$ of the connection region 142 at the proximal opening 152. Alternatively, the width $W_{con}$ of the connection region 142 at the distal opening 154 can be larger (e.g., as shown in the embodiment of FIG. 3) or smaller (e.g., as shown in the embodiment of FIGS. 4A-4C) than the width $W_{con}$ of the connection region 142 at the proximal opening 152.

As also illustrated in FIG. 2, the width of the isolation region 144 at the distal of opening 154 can be substantially the same as the width $W_{con}$ of the connection region 142 at the proximal opening 152. The width of the isolation region 144 at the distal opening 154 can thus of be in any of the below-identified ranges corresponding to the width $W_{con}$ of the connection region 142 at the proximal opening 152. Alternatively, the width of the isolation region 144 at the distal opening 154 can be larger (e.g., as shown in FIG. 3) or smaller (not shown) than the width $W_{con}$ of the connection region 142 at the proximal opening 152.

In some embodiments, the maximum velocity $V_{max}$ of a flow 212 in the flow channel 134 is substantially the same as the maximum velocity that the flow channel 134 can maintain without causing a structural failure in the respective microfluidic device (e.g., device 100) in which the flow channel is located. In general, the maximum velocity that a flow channel can maintain depends on various factors, including the structural integrity of the microfluidic device and the cross-sectional area of the flow channel. For the exemplary microfluidic devices disclosed and described herein, a maximum flow velocity $V_{max}$ in a flow channel having a cross-sectional area of about 3,500 to 10,000 square microns, is about 1.5 to 15 L/sec. Alternatively, the maximum velocity $V_{max}$ of a flow in a flow channel can be set so as to ensure that isolation regions are isolated from the flow in the flow channel. In particular, based on the width $W_{con}$ of the proximal opening of a connection region of an isolation chamber, $V_{max}$ can be set so as to ensure that the depth of penetration $D_p$ of a secondary flow into the connection region is less than $L_{con}$. For example, for an isolation chamber having a connection region with a proximal opening having a width $W_{con}$ of about 40 to 50 microns and $L_{con}$ of about 50 to 100 microns, $V_{max}$ can be set at or about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 μL/sec.

In some embodiments, the sum of the length $L_{con}$ of the connection region 142 and a corresponding length of the isolation region 144 of an isolation chamber 136, 138, 140 can be sufficiently short for relatively rapid diffusion of components of a second medium 204 contained in the isolation region 144 to a first medium 202 flowing or otherwise contained in the flow channel 134. For example, in some embodiments, the sum of (1) the length $L_{con}$ of the connection region 142 and (2) the distance between a biological micro-object located in isolation region 144 of an isolation chamber 136, 138, 140 and the distal opening 154 of the connection region can be one of the following ranges: from about 40 microns to 500 microns, 50 microns to 450 microns, 60 microns to 400 microns, 70 microns to 350 microns, 80 microns to 300 microns, 90 microns to 250 microns, 100 microns to 200 microns, or any range including one of the foregoing end points. The rate of diffusion of a molecule (e.g., an analyte of interest, such as an antibody) is dependent on a number of factors, including (without limitation) temperature, viscosity of the medium, and the coefficient of diffusion $D_0$ of the molecule. For example, the $D_0$ for an IgG antibody in aqueous solution at about 20° C. is about $4.4 \times 10^{-7}$ cm$^2$/sec, while the kinematic viscosity of cell culture medium is about $9 \times 10^{-4}$ m$^2$/sec. Thus, an antibody in cell culture medium at about 20° C. can have a rate of diffusion of about 0.5 microns/sec. Accordingly, in some embodiments, a time period for diffusion from a biological micro-object located in isolation region 144 into the flow channel 134 can be about 10 minutes or less (e.g., about 9, 8, 7, 6, 5 minutes, or less). The time period for diffusion can be manipulated by changing parameters that influence the rate of diffusion. For example, the temperature of the media can be increased (e.g., to a physiological temperature such as about 37° C.) or decreased (e.g., to about 15° C., 10° C., or 4° C.) thereby increasing or decreasing the rate of diffusion, respectively. Alternatively, or in addition, the concentrations of solutes in the medium can be increased or decreased.

The physical configuration of the isolation chamber 136 illustrated in FIG. 2 is but an example, and many other configurations and variations for isolation chambers are possible. For example, the isolation region 144 is illustrated as sized to contain a plurality of micro-objects 222, but the isolation region 144 can be sized to contain only about one, two, three, four, five, or similar relatively small numbers of micro-objects 222. Accordingly, the volume of an isolation region 144 can be, for example, at least about $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

As another example, the isolation chamber 136 is shown in FIG. 2 as extending generally perpendicularly from the flow channel 134 and thus forming generally about 90° angles with the flow channel 134. The isolation chamber 136 can alternatively extend from the flow channel 134 at other angles such as, for example, any angle from about 30° to about 150°.

As yet another example, the connection region 142 and the isolation region 144 are illustrated in FIG. 2 as having a substantially rectangular configuration, but one or both of the connection region 142 and the isolation region 144 can have a different configuration, including (without limitation) oval, triangular, circular, hourglass-shaped, and the like.

As still another example, the connection region 142 and the isolation region 144 are illustrated in FIG. 2 as having substantially uniform widths. That is, the width $W_{con}$ of the connection region 142 is shown as being uniform along the entire length $L_{con}$ from the proximal opening 152 to the distal opening 154. A corresponding width of the isolation region 144 is similarly uniform; and the width $W_{con}$ of the connection region 142 and a corresponding width of the isolation region 144 are shown as equal. However, in alternate embodiments, any of the foregoing can be different. For example, a width $W_{con}$ of the connection region 142 can vary along the length $L_{con}$, from the proximal opening 152 to the distal opening 154, e.g., in the manner of a trapezoid, or of an hourglass; a width of the isolation region 144 can also vary along the length $L_{con}$, e.g., in the manner of a triangle, or of a flask; and a width $W_{con}$ of the connection region 142 can be different than a width of the isolation region 144.

FIG. 3 illustrates an alternate embodiment of an isolation chamber 336, demonstrating some examples of the foregoing variations. While the alternative isolation chamber 336 is described as a replacement for chamber 136 in the microfluidic device 100, it should be appreciated that the isolation chamber 336 can replace any of isolation chambers in any of the microfluidic device embodiments disclosed or described herein. Furthermore, there may be one isolation chamber 336 or a plurality of isolation chambers 336 provided in a given microfluidic device.

The isolation chamber 336 includes a connection region 342 and an isolation structure 346 comprising an isolation region 344. The connection region 342 has a proximal opening 352 to the flow channel 134 and a distal opening 354 to the isolation region 344. In the embodiment illustrated in FIG. 3, the connection region 342 expands such that its width $W_{con}$ increases along a length of the connection region $L_{con}$, from the proximal opening 352 to the distal opening 354. Other than having a different shape, however, the connection region 342, isolation structure 346, and isolation region 344 function generally the same as the above-described connection region 142, isolation structure 146, and isolation region 144 of isolation chamber 136 shown in FIG. 2.

For example, the flow channel 134 and the isolation chamber 336 can be configured so that the maximum penetration depth $D_p$ of the secondary flow 214 extends into the connection region 342, but not into the isolation region 344. The length $L_{con}$ of the connection region 342 can thus be greater than the maximum penetration depth $D_p$, generally as discussed above with respect to the connection regions 142 shown in FIG. 2. Also, as discussed above, micro-objects 222 in the isolation region 344 will stay in the isolation region 344 as long as the velocity of the flow 212 in the flow channel 134 does not exceed the maximum flow velocity $V_{max}$. The flow channel 134 and connection region 342 are thus examples of swept (or flow) regions, and the isolation region 344 is an example of an unswept (or non-flow) region.

FIGS. 4A-C depict another exemplary embodiment of a microfluidic device 400 containing a microfluidic circuit 432 and flow channels 434, which are variations of the respective microfluidic device 100, circuit 132 and flow channel 134 of FIGS. 1A-1C. The microfluidic device 400 also has a plurality of isolation chambers 436 that are additional variations of the above-described isolation chambers 136, 138, 140 and 336. In particular, it should be appreciated that the isolation chambers 436 of device 400 shown in FIGS. 4A-C can replace any of the above-described isolation chambers 136, 138, 140, 336 in devices 100 and 300. Likewise, the microfluidic device 400 is another variant of the microfluidic device 100, and may also have the same or a different DEP configuration as the above-described microfluidic device 300, as well as any of the other microfluidic system components described herein.

The microfluidic device 400 of FIGS. 4A-C comprises a support structure (not visible in FIGS. 4A-C, but can be the same or generally similar to the support structure 104 of device 100 depicted in FIGS. 1A-1C), a microfluidic circuit structure 412, and a cover (not visible in FIGS. 4A-C, but can be the same or generally similar to the cover 122 of device 100 depicted in FIGS. 1A-1C). The microfluidic circuit structure 412 includes a frame 414 and microfluidic circuit material 416, which can be the same as or generally similar to the frame 114 and microfluidic circuit material 116 of device 100 shown in FIGS. 1A-1C. As shown in FIG. 4A, the microfluidic circuit 432 defined by the microfluidic circuit material 416 can comprise multiple flow channels 434 (two are shown but there can be more) to which multiple isolation chambers 436 are fluidically connected.

Each isolation chamber 436 can comprise an isolation structure 446, an isolation region 444 within the isolation structure 446, and a connection region 442. From a proximal opening 472 at the flow channel 434 to a distal opening 474 at the isolation structure 436, the connection region 442 fluidically connects the flow channel 434 to the isolation region 444. Generally in accordance with the above discussion of FIG. 2, a flow 482 of a first fluidic medium 402 in a flow channel 434 can create secondary flows 484 of the first medium 402 from the flow channel 434 into and/or out of the respective connection regions 442 of the isolation chambers 436.

As illustrated in FIG. 4B, the connection region 442 of each isolation chamber 436 generally includes the area extending between the proximal opening 472 to a flow channel 434 and the distal opening 474 to an isolation structure 446. The length $L_{con}$ of the connection region 442 can be greater than the maximum penetration depth $D_p$ of secondary flow 484, in which case the secondary flow 484 will extend into the connection region 442 without being redirected toward the isolation region 444 (as shown in FIG. 4A). Alternatively, at illustrated in FIG. 4C, the connection region 442 can have a length $L_{con}$ that is less than the maximum penetration depth $D_p$, in which case the secondary flow 484 will extend through the connection region 442 and be redirected toward the isolation region 444. In this latter situation, the sum of lengths $L_{c1}$ and $L_{c2}$ of connection region 442 is greater than the maximum penetration depth $D_p$, so that secondary flow 484 will not extend into isolation region 444. Whether length $L_{con}$ of connection region 442 is greater than the penetration depth $D_p$, or the sum of lengths $L_{c1}$ and $L_{c2}$ of connection region 442 is greater than the penetration depth $D_p$, a flow 482 of a first medium 402 in flow channel 434 that does not exceed a maximum velocity $V_{max}$ will produce a secondary flow having a penetration depth $D_p$, and micro-objects (not shown but can be the same or generally similar to the micro-objects 222 shown in FIG. 2) in the isolation region 444 of an isolation chamber 436 will not be drawn out of the isolation region 444 by a flow 482 of first medium 402 in flow channel 434. Nor will the flow 482 in flow channel 434 draw miscellaneous materials (not shown) from flow channel 434 into the isolation region 444 of an isolation chamber 436. As such, diffusion is the only mechanism by which components in a first medium 402 in the flow channel 434 can move from the flow channel 434 into a second medium 404 in an isolation region 444 of an isolation chamber 436. Likewise, diffusion is the only mechanism by which components in a second medium 404 in an isolation region 444 of an isolation chamber 436 can move from the isolation region 444 to a first medium 402 in the flow channel 434. The first medium 402 can be the same medium as the second medium 404, or the first medium 402 can be a different medium than the second medium 404. Alternatively, the first medium 402 and the second medium 404 can start out being the same, then become different, e.g., through conditioning of the second medium by one or more cells in the isolation region 444, or by changing the medium flowing through the flow channel 434.

As illustrated in FIG. 4B, the width $W_{ch}$ of the flow channels 434 (i.e., taken transverse to the direction of a fluid medium flow through the flow channel indicated by arrows 482 in FIG. 4A) in the flow channel 434 can be substantially perpendicular to a width $W_{con1}$ of the proximal opening 472 and thus substantially parallel to a width $W_{con2}$ of the distal opening 474. The width $W_{con1}$ of the proximal opening 472 and the width $W_{con2}$ of the distal opening 474, however, need not be substantially perpendicular to each other. For example, an angle between an axis (not shown) on which the width $W_{con1}$ of the proximal opening 472 is oriented and another axis on which the width $W_{con2}$ of the distal opening 474 is oriented can be other than perpendicular and thus other than 90°. Examples of alternatively angles include angles in any of the following ranges: from about 30° to about 90°, from about 45° to about 90°, from about 60° to about 90°, or the like.

In various embodiments of isolation chambers 136, 138, 140, 336, or 436, the isolation region of the isolation chamber may have a volume configured to support no more than about $1\times10^3$ $5\times10^2$ $4\times10^2$ $3\times10^2$ $2\times10^2$ $1\times10^2$, 50, 25, 15, or 10 cells in culture. In other embodiments, the isolation region of the isolation chamber has a volume to support up to and including about $1\times10^3$, $1\times10^4$, or $1\times10^5$ cells.

In various embodiments of isolation chambers 136, 138, 140, 336, or 436, the width $W_{ch}$ of the flow channel 134 at a proximal opening 152 (isolation chambers 136, 138, or 14); the width $W_{ch}$ of the flow channel 134 at a proximal opening 352 (isolation chambers 336); or the width $W_{ch}$ of the flow channel 434 at a proximal opening 472 (isolation chambers 436) can be any of the following ranges: from about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the flow channel 134 or 434 can be in other ranges (e.g., a range defined by any of the endpoints listed above).

In various embodiments of isolation chambers 136, 138, 140, 336, or 436, the height $H_{ch}$ of the flow channel 134 at a proximal opening 152 (isolation chambers 136, 138, or 140), the flow channel 134 at a proximal opening 352 (isolation chambers 336), or the flow channel 434 at a proximal opening 472 (isolation chambers 436) can be any of the following ranges: from about 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the flow channel 134 or 434 can be in other ranges (e.g., a range defined by any of the endpoints listed above).

In various embodiments of isolation chambers 136, 138, 140, 336, or 436, a cross-sectional area of the flow channel 134 at a proximal opening 152 (isolation chambers 136, 138, or 140), the flow channel 134 at a proximal opening 352 (isolation chambers 336), or the flow channel 434 at a proximal opening 472 (isolation chambers 436) can be any of the following ranges: from about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the flow channel 134 at a proximal opening 152, the flow channel 134 at a proximal opening 352, or the flow channel 434 at a proximal opening 472 can be in other ranges (e.g., a range defined by any of the endpoints listed above).

In various embodiments of isolation chambers 136, 138, 140, 336, or 436, the length of the connection region $L_{con}$ can be any of the following ranges: from about 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 142 (isolation chambers 136, 138, or 140), connection region 342 (isolation chambers 336), or connection region 442 (isolation chambers 436) can be in a different ranges than the foregoing examples (e.g., a range defined by any of the endpoints listed above).

In various embodiments of isolation chambers 136, 138, 140, 336, or 436, the width $W_{con}$ of a connection region 142 at a proximal opening 152 (isolation chambers 136, 138, or 140, connection region 342 at a proximal opening 352 (isolation chambers 336), or a connection region 442 at a proximal opening 472 (isolation chambers 436) can be any of the following ranges: from about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 142 at a proximal opening 152; connection region 342 at a proximal opening 352; or a connection region 442 at a proximal opening 472 can be different than the foregoing examples (e.g., a range defined by any of the endpoints listed above).

In various embodiments of isolation chambers 136, 138, 140, 336, or 436, the width $W_{con}$ of a connection region 142 at a proximal opening 152 (isolation chambers 136, 138, or 140), a connection region 342 at a proximal opening 352 (isolation chambers 336), or a connection region 442 at a proximal opening 472 (isolation chambers 436) can be any of the following ranges: from about 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 142 at a proximal opening 152, a connection region 342 at a proximal opening 352, or a connection region 442 at a proximal opening 472 can be different than the foregoing examples (e.g., a range defined by any of the endpoints listed above).

In various embodiments of isolation chambers 136, 138, 140, 336, or 436, a ratio of the length $L_{con}$ of a connection region 142 to a width $W_{con}$ of the connection region 142 at the proximal opening 152 (isolation chambers 136, 138, or 140), a ratio of the length $L_{con}$ of a of connection region 342 to a width $W_{con}$ of the connection region 342 at the proximal opening 352 (isolation chambers 336), or a ratio of the length $L_{con}$ of a connection region 442 to a width $W_{con}$ of the connection region a connection region 442 to a width $W_{con}$ of the connection region 442 at the proximal opening 472 (isolation chambers 436) can be greater than or equal to any of the following ratios: about 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 142 to a width $W_{con}$ of the connection region 142 at the proximal opening 152, the ratio of the length $L_{con}$ of a connection region 342 to a width $W_{con}$ of the connection region 342 at the proximal opening 372; or the ratio of the length $L_{con}$ of a connection region 442 to a width $W_{con}$ of the connection region 442 at the proximal opening 472 can be different than the foregoing examples.

In various embodiments of microfluidic devices having isolation chambers 136, 138, 140, 336, or 436, $V_{max}$ can be set at about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 µL/sec.

In various embodiments of microfluidic devices having isolation chambers 136, 138, 140, 336, or 436, the volume of an isolation region 144 (isolation chambers 136, 138, or 140), 344 (isolation chambers 336) or 444 (isolation chambers 436) can be, for example, at least about $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more.

In some embodiments, the microfluidic device has isolation chambers 136, 138, 140, 336, or 436, wherein no more than about $1\times10^2$ biological cells may be maintained, and the volume of the isolation chambers may be no more than about $2\times10^6$ cubic microns.

In some embodiments, the microfluidic device has isolation chambers 136, 138, 140, 336, or 436, wherein no more than about $1\times10^2$ biological cells may be maintained, and the volume of the isolation chambers may be no more than about $4\times10^5$ cubic microns.

In yet other embodiments, the microfluidic device has isolation chambers 136, 138, 140, 336, or 436, wherein no more than about 50 biological cells may be maintained, and the volume of the isolation chambers may be no more than about $4\times10^5$ cubic microns.

In various embodiment, the microfluidic device has isolation chambers configured as in any of the embodiments discussed herein where the microfluidic device has about 100 to about 500 isolation chambers; about 200 to about 1000 isolation chambers, about 500 to about 1500 chambers, about 1000 to about 2000 isolation chambers, or about 1000 to about 3500 isolation chambers.

In some other embodiments, the microfluidic device has isolation chambers configured as in any of the embodiments discussed herein where the microfluidic device has about 1500 to about 3000 isolation chambers, about 2000 to about 3500 isolation chambers, about 2000 to about 4000 isolation chambers, about 2500 to about 4000 isolation chambers, or about 3000 to about 4500 isolation chambers.

In some embodiments, the microfluidic device has isolation chambers configured as in any of the embodiments discussed herein where the microfluidic device has about 3000 to about 4500 isolation chambers, about 3500 to about 5000 isolation chambers, about 4000 to about 5500 chambers, about 4500 to about 6000 isolation chambers or about 5000 to about 6500 chambers.

In further embodiments, the microfluidic device has isolation chambers configured as in any of the embodiments discussed herein, where the microfluidic device has about 6000 to about 7500 isolation chambers, about 7000 to about 8500 isolation chambers, about 8000 to about 9500 isolation chambers, about 9000 to about 10,500 isolation chambers, about, about 10,000 to about 11,500 isolation chambers, about 11,000 to about 12,500 isolation chambers, about 12,000 to about 13,500 isolation chambers, about 13,000 to about 14,500 isolation chambers about 14,000 to about 15,500 isolation chambers, about 15,000 to about 16,500 isolation chambers, about 16,000 to about 17,500 isolation chambers, about 17,000 to about 18,500 isolation chambers.

In various embodiments, the microfluidic device has isolation chambers configured as in any of the embodiments discussed herein, where the microfluidic device has about 18,000 to about 19,500 isolation chambers, about 18,500 to about 20,000 isolation chambers, about 19,000 to about 20,500 isolation chambers, about 19,500 to about 21,000 isolation chambers, or about 20,000 to about 21,500 isolation chambers.

Other Properties of the Isolation Chambers.

Although the barriers of microfluidic circuit material 116 (FIGS. 1A-1C) and 416 (FIGS. 4A-4C) that define the respective isolation chambers 136, 138, 140 of device 100 (FIGS. 1A-1C) and form the isolation structure 446 of isolation chambers 436 of device 400 (FIGS. 4A-4C) are illustrated and discussed above as physical barriers, it should be appreciated that the barriers can alternatively be created as "virtual" barriers comprising DEP forces activated by light in the light pattern 322.

In some other embodiments, respective isolation chambers 136, 138, 140, 336 and 436 can be shielded from illumination (e.g., by the detector and/or the selector control module directing the light source 320), or can be only selectively illuminated for brief periods of time. Cells and other biological micro-objects contained in the isolation chambers can thus be protected from further (i.e., possibly hazardous) illumination after being moved into the isolation chambers 136, 138, 140, 336 and 436.

Fluidic Medium.

With regard to the foregoing discussion about microfluidic devices having a flow channel and one or more isolation chambers, a fluidic medium (e.g., a first medium and/or a second medium) can be any fluid that is capable of maintaining a biological micro-object in a substantially assayable state. The assayable state will depend on the biological micro-object and the assay being performed. For example, if the biological micro-object is a cell that is being assayed for the secretion of a protein of interest, the cell would be substantially assayable provided that the cell is viable and capable of expressing and secreting proteins.

Processing and Storing Biological Cells.

FIG. 5A shows multiple stacks of (prior art) microtiter well plates used for holding and storing (e.g., when freezing) biological cells. As mentioned above, microtiter well plates do not interface well with microfluidic devices. Moreover, they are relatively large and thus occupy large amounts of costly freezer space, and require a significant amount of costly cell preservation reagents when they are used for the storage and archiving of biological cells. By way of comparison, FIG. 5B is a picture of an exemplary microfluidic device constructed in accordance with the disclosed embodiments herein.

More particularly, the infrastructure of the microfluidic device illustrated and described in detail herein), lends itself to being a much more efficient storage vessel for biological cells, especially since the same microfluidic device can be used for downstream experiments and analysis of the cells e.g., sequencing, culturing, expansion/cloning/subcloning, assaying, etc. (hereinafter collectively referring to as "testing"). In particular, after a sample has been initially processed in a microfluidic device, including the sequestration of biological cells into the respective isolation regions of the isolation chambers (e.g., isolation chambers 136, 138 and 140 of device 100 shown in above-described FIGS. 1A-1C, an inventory (or library) of the sequestered cells may be created and stored in a storage medium associated with the microfluidic device, and the device may thereafter be cooled and stored (whether for days, weeks, months or even years) in a subzero storage freezer, until there is a need for testing of the sequestered cells.

Figure 6:
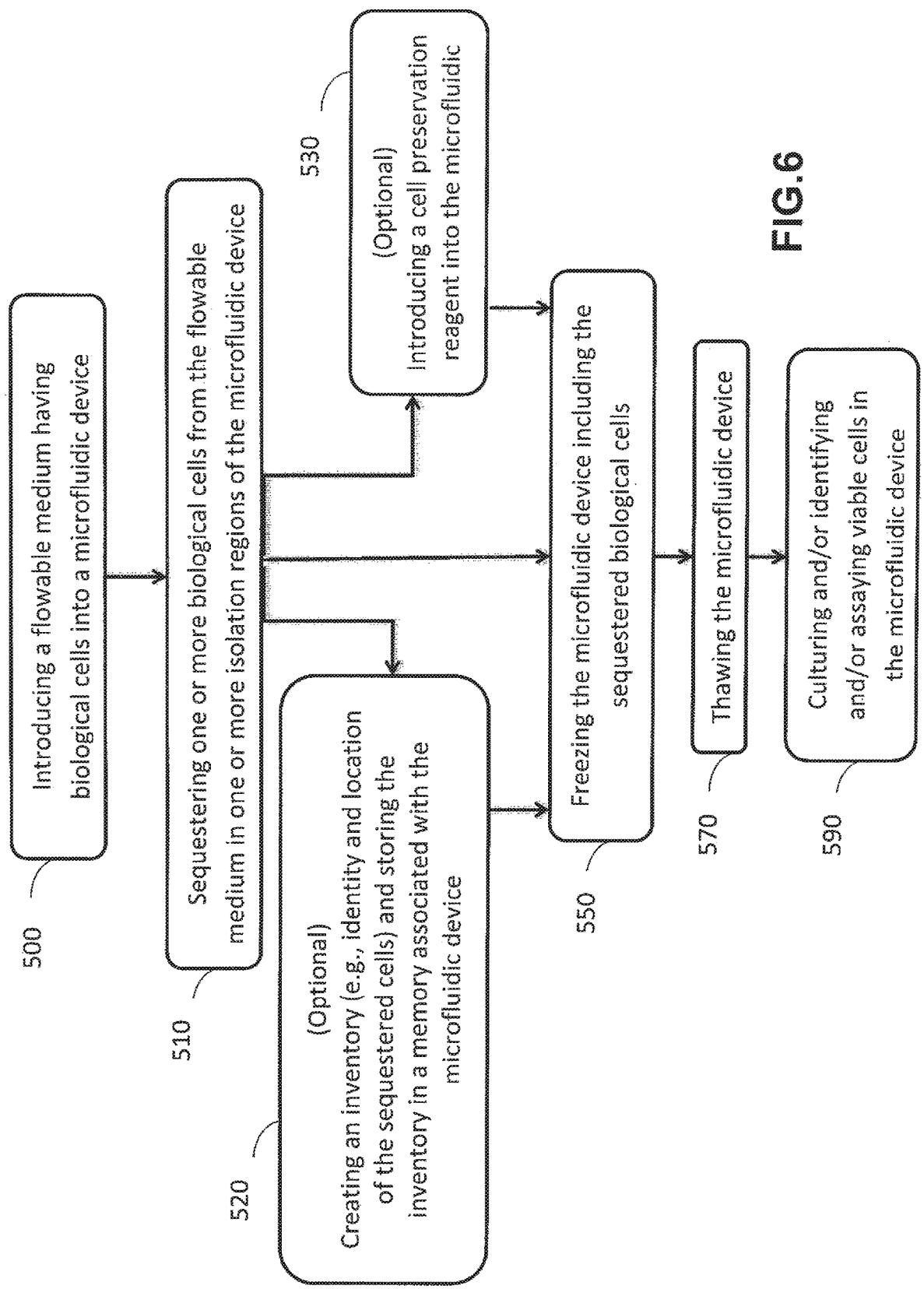
FIG. 6 is a schematic flow diagram of an exemplary method of processing, storing (by freezing), thawing and further processing biological cells in a microfluidic device.

Towards this end, and with reference to FIG. 6, an exemplary method for processing and storing biological cells in a microfluidic device includes, at step 500, introducing a flowable medium into a microfluidic device, the flowable medium including biological cells. At step 510, one or more biological cells from the flowable medium are sequestered in one or more isolation regions of the microfluidic device. At step 550, the microfluidic device is frozen for storage, including the one or more biological cells sequestered therein.

Cellular Expansion Prior to Freezing.

While as few as a single biological cell may be initially sequestered within the microfluidic device, more typically at least a single cell will be sequestered in each of a plurality of isolation regions within the microfluidic device. A typical microfluidic device used in embodiments of the method may have anywhere from dozens, to hundreds or more isolation regions, with each isolation region having a volume (without limitation) in a range of about $1.5 \times 10^5$ cubic microns to about $1.5 \times 10^6$ cubic microns, and thus be capable of sequestering as many as about 10 cells to about 50 cells, or more. In one embodiment, prior to freezing the microfluidic device, one or more of the sequestered ("starting") cells in a first isolation region of the microfluidic device is cultured to generate a plurality of "new" cells in the first isolation region adequate in number so that at least one viable cell will be present in the first isolation region after thawing the microfluidic device.

Towards this end, it may be desirable to allow sufficient culturing to accumulate at least eight biological cells in each isolation chamber of interest prior to freezing the device, and more preferably to accumulate at least ten, sixteen, twenty, twenty-four, thirty, or forty biological cells in each isolation chamber of interest prior to freezing the device. In some cases, it may be preferable to accumulate an even greater number of cells in each isolation region of interest prior to freezing the device, including in some embodiments having adequately sized isolation chambers in the microfluidic device, accumulating anywhere from fifty, sixty, seventy, eighty, ninety, or even one hundred or more cells in each of the isolation regions of interest prior to freezing. Methods of expanding biological cells within the presently disclosed microfluidic devices have been described in U.S. patent application Ser. No. 15/135,707, filed on Apr. 22, 2016, the entire contents of which are incorporated herein by reference.

Blocking Solutions and Blocking Agents.

Without intending to be limited by theory, after cells are frozen and then thawed, there is a high incidence level of cell lysis and, as a result, the interior surfaces of the microfluidic device can be fouled (e.g., due to the cellular contents of the lyse cell(s), including proteins, nucleic acids, and other biological molecules, adhering to the interior surfaces of the microfluidic device, particularly the substrate surface) and can result in non-lysed cells adhering or "sticking" to the fouled inner surfaces of the microfluidic device. In some embodiments, one or more of the inner surfaces of the microfluidic device (e.g. the inner surface of the electrode activation substrate of a DEP-configured microfluidic device, the cover of the microfluidic device, and/or the surfaces of the circuit material) are treated with a blocking solution and/or blocking agent to prevent or reduce cell adherence or sticking. In some embodiments, the cells that are to be frozen in the microfluidic device are imported in a blocking solution that includes one or more blocking agents.

In other embodiments, the inner surface(s) of the microfluidic device (e.g., a DEP-configured microfluidic device) are treated or "primed" with a blocking solution comprising a blocking agent prior to introduction of the cells into the microfluidic device. Any convenient blocking agent/blocking solution can be used, including but not limited to: serum or serum factors, bovine serum albumin (BSA), polymers, detergents, enzymes, and any combination thereof. In some specific embodiments, a blocking agent will be used to treat the inner surface(s) of the microfluidic device. In one example, a polymer comprising alkylene ether moieties can be included as a blocking agent in the blocking solution. A wide variety of alkylene ether containing polymers may be suitable. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a conditioned surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. In another example, DNase can be included in the blocking agent in a blocking solution to remove extranuclear DNA that might cause sticking to the substrate and/or walls of the microfluidic device.

In some embodiments, a blocking solution can comprise various proteins and/or peptides as blocking agents. In a specific embodiment, a blocking solution that finds use in the present disclosure includes a protein such as albumin (e.g. BSA) and/or serum (or a combination of multiple different sera) comprising albumin and/or one or more other similar proteins as blocking agents. The serum can be from any convenient source, including but not limited to fetal calf serum, sheep serum, goat serum, horse serum, and the like. In certain embodiments, BSA in a blocking solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a blocking solution is present in a range of from about 20% (v/v) to about 50% v/v, including 25%, 30%, 35%, 40%, 45%, or more or anywhere in between. In some embodiments, BSA is present as a blocking agent in a blocking solution at 5 mg/mL, whereas in other embodiments, BSA is present as a blocking agent in a blocking solution at 70 mg/mL. In certain embodiments, serum is present as a blocking agent in a blocking solution at 30%.

Coating Materials.

Depending on the embodiment, any of the foregoing blocking agents/blocking solutions can be replaced by or used in combination with various coating materials used to coat one or more of the inner surface(s) of the microfluidic device (e.g., a DEP-configured and/or EW-configured microfluidic device). In some embodiments, at least one surface of the microfluidic device includes a coating material that reducing surface fouling and/or prevents or reduces cells from sticking to the surface. In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Polymer-Based Coating Materials.

The at least one inner surface may include a coating material that comprises a polymer. The polymer may be covalently or non-covalently bound (or linked) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA).

In other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. These latter exemplary polymers are polyelectrolytes and may alter the characteristics of the surface to deter cell sticking.

In some embodiments, the coating material may include a polymer containing urethane moieties, such as, but not limited to polyurethane.

In other embodiments, the coating material may include a polymer containing phosphate moieties, either at a terminus of the polymer backbone or pendant from the backbone of the polymer.

In other embodiments, the coating material may include a polymer containing saccharide moieties. In a non-limiting example, polysaccharides such as those derived from algal or fungal polysaccharides such as xanthan gum or dextran may be suitable to form a material which may reduce or prevent cell sticking in the microfluidic device. For example, a dextran polymer having a size about 3 Kda may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation. A nucleic acid containing polymer may include a polyelectrolyte which may reduce or prevent cell sticking.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA). In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In further embodiments, the coating material may include a polymer including amine moieties. The polyamino polymer may include a natural polyamine polymer or a synthetic polyamine polymer. Examples of natural polyamines include spermine, spermidine, and putrescine.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that reduce surface fouling and/or prevent or reduce cell sticking to the surface the microfluidic device. The covalently linked molecules include a linking group, wherein the linking group is covalently linked to a surface of the microfluidic device. The linking group is also covalently linked to a moiety configured to reduce surface fouling and/or prevent or reduce cell sticking to the surface the microfluidic device. The surface to which the linking group links may include a surface of the substrate of the microfluidic device which, for embodiments in which the microfluidic device includes a DEP configuration, can include silicon and/or silicon dioxide. In some embodiments, the covalently linked coating materials coat substantially all of the inner surfaces of the microfluidic device.

In some embodiments, the covalently linked moiety configured to reduce surface fouling and/or prevent or reduce cell sticking to the surface the microfluidic device may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The covalently linked moiety configured to reduce surface fouling and/or prevent or reduce cell sticking to the surface the microfluidic device may be any polymer as described herein, and may include one or more polymers containing alkylene oxide moieties, carboxylic acid moieties, saccharide moieties, sulfonic acid moieties, phosphate moieties, amino acid moieties, nucleic acid moieties, or amino moieties.

In other embodiments, the covalently linked moiety configured to reduce surface fouling and/or prevent or reduce cell sticking to the surface the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety.

In some embodiments, the covalently linked moiety may be an alkyl group that comprises carbon atoms that form a linear chain (e.g., a linear chain of at least 10 carbons, or at least 14, 16, 18, 20, 22, or more carbons). Thus, the alkyl group may be an unbranched alkyl. In some embodiments, the alkyl group may include a substituted alkyl group (e.g., some of the carbons in the alkyl group can be fluorinated or perfluorinated). The alkyl group may comprise a linear chain of substituted (e.g., fluorinated or perfluorinated) carbons joined to a linear chain of non-substituted carbons. For example, the alkyl group may include a first segment, which may include a perfluoroalkyl group, joined to a second segment, which may include a non-substituted alkyl group. The first and second segments may be joined directly or indirectly (e.g., by means of an ether linkage). The first segment of the alkyl group may be located distal to the linking group, and the second segment of the alkyl group may be located proximal to the linking group. In other embodiment, the alkyl group may include a branched alkyl group and may further have one or more arylene group interrupting the alkyl backbone of the alkyl group. In some embodiments, a branched or arylene-interrupted portion of the alkyl or fluorinated alkyl group is located at a point distal to the linking group and the covalent linkage to the surface.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having covalently charged moieties attached to an alkyl or fluoroalkyl chain having a greater number of methylene or fluoromethylene units. In some embodiments, the coating material having more than one kind of covalently linked moiety may be designed such that a first set of molecules which have a greater number of backbone atoms, and thus a greater length from the covalent attachment to the surface, may provide capacity to present bulkier moieties at the coated surface, while a second set of molecules having different, less sterically demanding termini and fewer backbone atoms can help to functionalize the entire substrate surface and thereby prevent undesired adhesion or contact with silicon or alumina making up the substrate itself. In another example, the covalently linked moieties may provide a zwitterionic surface presenting alternating charges in a random fashion on the surface.

Conditioned Surface Properties.

In some embodiments, the covalently linked moieties may form a monolayer when covalently linked to the surface of the microfluidic device (e.g., a DEP configured substrate surface). In some embodiments, the conditioned surface formed by the covalently linked moieties may have a thickness of less than 10 nm (e.g., less than 5 nm, or about 1.5 to 3.0 nm). In other embodiments, the conditioned surface formed by the covalently linked moieties may have a thickness of about 10 nm to about 50 nm. In some embodiments, the conditioned surface does not require a perfectly formed monolayer to be suitably functional for operation within a DEP-configured microfluidic device.

In various embodiments, the coating material of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

Aside from the composition of the coating material, other factors such as physical (and electrical) thickness of the coating material can impact the generation of DEP force and/or electrowetting force by a substrate in a microfluidic device. Various factors can alter the physical and electrical thickness of the coating material, including the manner in which the coating material is deposited on the substrate (e.g. vapor deposition, liquid phase deposition, spin coating, or electrostatic coating). The physical thickness and uniformity of the coating material can be measured using an ellipsometer.

Besides their electrical properties, the coating material may have properties that are beneficial in use with biological molecules. For example, coating materials that contain fluorinated (or perfluorinated) alkyl groups may provide a benefit relative to unsubstituted alkyl groups in reducing the amount of surface fouling. Surface fouling, as used herein, refers to the amount of material indiscriminately deposited on the surface of the microfluidic device, which may include permanent or semi-permanent deposition of biomaterials such as protein and degradation products, nucleic acids, and respective degradation products. Such fouling can increase the amount of adhesion of biological micro-objects to the surface.

Various electrical and functional properties for different coating materials that can be used in microfluidic devices are included in the table below.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). The physical thickness and uniformity of the conditioned surface can be measured using an ellipsometer.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Various properties for conditioned surfaces which may be used in DEP configurations are included in the table below. As can be seen, for entries 1 to 7, which were all covalently linked conditioned surfaces as described herein, the thickness as measured by ellipsometry were consistently thinner than that of entry 8, a CYTOP surface which was formed by non-covalent spin coating (N/A represents data not available throughout the table). Fouling was found to be more dependent upon the chemical nature of the surface than upon the mode of formation as the fluorinated surfaces were typically less fouling than that of alkyl (hydrocarbon) conditioned surfaces.

TABLE 1

Properties of various conditioned surfaces prepared by covalently modifying a surface, compared to CYTOP, a non-covalently formed surface.

| Surface modification type | Formula of surface modifying reagent | Thickness | Fouling |
|---|---|---|---|
| Alkyl terminated siloxane ($C_{16}$) | $CH_3-(CH_2)_{15}-Si-(OCH_3)_3$ | N/A | More fouling than fluorinated layers. |
| Alkyl terminated siloxane ($C_{18}$) | $CH_3-(CH_2)_{17}-Si-(OCH_3)_3$ | ~2 nm | More fouling than fluorinated layers. |

TABLE 1-continued

Properties of various conditioned surfaces prepared by covalently modifying a surface, compared to CYTOP, a non-covalently formed surface.

| Surface modification type | Formula of surface modifying reagent | Thickness | Fouling |
|---|---|---|---|
| Alkyl-terminated phosphonate ester $C_{18}PA$ | $CH_3-(CH_2)_{17}-P=O(OH)2$ | N/A | More fouling than fluorinated layers. |
| Alkyl terminated siloxane ($C_{22}$) | $CH_3-(CH_2)_{21}-Si-(OCH_2CH_3)_3$ | ~2-2.5 nm | More fouling than fluorinated layers. |
| Fluoro-alkyl-terminated alkyl-siloxane $C_{10}F$ | $CF_3-(CF_2)_7-(CH_2)_2-Si-(OCH_3)_3$ | ~1 nm | More resistant to fouling than alkyl-terminated layers |
| Fluoro-alkyl-terminated alkyl-siloxane ($C_{16}F$) | $CF_3-(CF_2)_{13}-(CH_2)_2-Si-(OCH_3)_3$ | ~2 nm | More resistant to fouling than alkyl-terminated layers |
| Fluoro-alkyl-terminated alkoxy-alkyl-siloxane $C_6FC_{13}$ | $CF_3-(CF_2)_5-(CH_2)_2-O-(CH_2)_{11}-Si(OCH_3)_3$ | ~2 nm | N/A |
| CYTOP Fluoropolymer [1, 2] | | ~30 nm | More resistant to fouling than alkyl-terminated layers |

1. CYTOP structure: 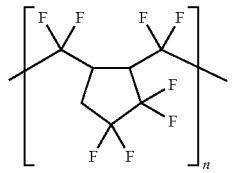
2. Spin coated, not covalent.

Linking Group to Surface.

The covalently linked moieties forming the coating material are attached to the surface via a linking group. The linking group may be a siloxy linking group formed by the reaction of a siloxane-containing reagent with oxides of the substrate surface, which can include silicon oxide (e.g., for a DEP-configured substrate) or aluminum oxide or hafnium oxide (e.g., for a EW-configured substrate). In some other embodiments, the linking group may be a phosphonate ester formed by the reaction of a phosphonic acid containing reagent with the oxides of the substrate surface.

Multi-Part Conditioned Surface.

The covalently linked coating material may be formed by reaction of a molecule which already contains the moiety configured to reduce surface fouling and/or prevent or reduce cell sticking to the surface the microfluidic device (e.g., an alkyl siloxane reagent or a fluoro-substituted alkyl siloxane reagent, which may include a perfluoroalkyl siloxane reagent), as is described below. Alternatively, the covalently linked coating material may be formed by coupling the moiety configured to reduce surface fouling and/or prevent or reduce cell sticking to a surface modifying ligand that itself is covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1.

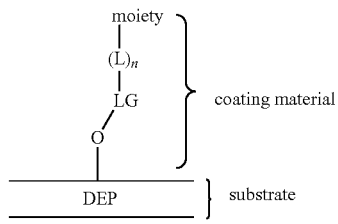

Formula 1

The coating material may be linked covalently to oxides of the surface of a DEP-configured substrate. The DEP-configured substrate may comprise silicon or alumina or hafnium oxide, and oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to reduce surface fouling and/or prevent or reduce cell sticking to the surface the microfluidic device can be any of the moieties described herein. The linking group LG may be directly or indirectly connected to the moiety configured to reduce surface fouling and/or prevent or reduce cell sticking to the surface the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, in some non-limiting examples. Additionally, the linker L may have one or more arylene, heteroarylene, or heterocyclic groups interrupting the backbone of the linker. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety configured to reduce surface fouling and/or prevent or reduce cell sticking to the surface the microfluidic device is added to the surface of the substrate in a one step process, a molecule of Formula 2 may be used to introduce the coating material:

$$\text{moiety-(L)}_n\text{-LG.} \qquad \text{Formula 2}$$

In some embodiments, the moiety configured to reduce surface fouling and/or prevent or reduce cell sticking to the surface the microfluidic device may be added to the surface of the substrate in a multi-step process. When the moiety configured to reduce surface fouling and/or prevent or reduce cell sticking is coupled to the surface in a step wise fashion, the linker L may further include a coupling group CG, as shown in Formula 3.

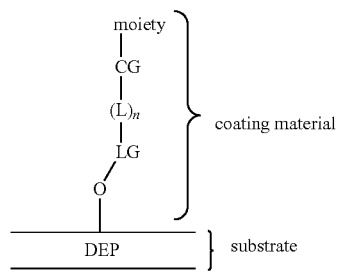

Formula 3

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to reduce surface fouling and/or prevent or reduce cell sticking to the surface the microfluidic device) of a linker L. In some other embodiments, the coupling group CG may interrupt the backbone of the linker L. In some embodiments, the coupling group CG is triazolylene, which is the result of a reaction between an alkyne group and an azide group, either of which may be the reactive moiety $R_x$ or the reactive pairing moiety $R_{px}$, as is known in the art for use in Click coupling reactions. A triazolylene group may also be further substituted. For example, a dibenzocylcooctenyl fused triazolylene group may result from the reaction of a moiety bound to a dibenzocyclooctynyl reactive pairing moiety $R_{px}$ with an azido reactive moiety $R_x$ of the surface modifying molecule, which are described in more detail in the following paragraphs. A variety of dibenzocyclooctynyl modified molecules are known in the art or may be synthesized to incorporate a moiety configured to support cell growth, viability, portability, or any combination thereof.

When the coating material is formed in a multi-step process, the moiety configured to reduce surface fouling and/or prevent or reduce cell sticking to the surface the microfluidic device may be introduced by reaction of a moiety-containing reagent (Formula 5) with a substrate having a surface modifying ligand covalently linked thereto (Formula 6).

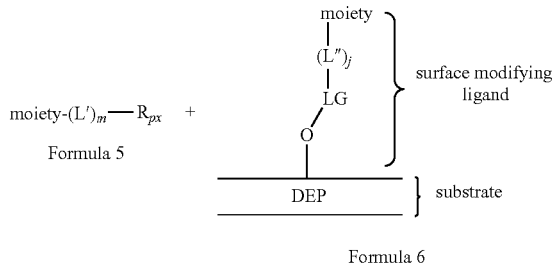

Formula 6

The modified surface of Formula 4 has a surface modifying ligand attached thereto, which has a formula of -LG-(L")j-$R_x$, which is linked to the oxide of the substrate and is formed similarly as described above for the conditioned surface of Formula 1. The surface of the substrate can be a DEP-configured substrate surface as described above, and can include oxides either native to the substrate or introduced therein. The linking group LG is as described above. A linker L" may be present (j=1) or absent (j=0). The linker L" may have a linear portion where a backbone of the linear portion may include 1 to 100 non-hydrogen atoms selected from any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker. In some embodiments, the backbone of the linker L" may include 10 to 20 carbon atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

A reactive moiety $R_x$ is present at the terminus of the surface modifying ligand distal to the covalent linkage of the surface modifying ligand with the surface. The reactive moiety $R_x$ is any suitable reactive moiety useful for coupling reactions to introduce the moiety configured to reduce surface fouling and/or prevent or reduce cell sticking to the surface the microfluidic device. In some embodiments, the reactive moiety $R_x$ may be an azido, amino, bromo, a thiol, an activated ester, a succinimidyl or alkynyl moiety.

Moiety-Containing Reagent.

The moiety-containing reagent (Formula 5) is configured to supply the moiety configured to reduce surface fouling and/or prevent or reduce cell sticking to the surface the microfluidic device.

Moiety-(L')$_m$-R$_{px}$                Formula 5

The moiety configured to reduce surface fouling and/or prevent or reduce cell sticking to the surface the microfluidic device of the moiety-containing reagent is linked to the surface modifying ligand by reaction of a reactive pairing moiety $R_{px}$ with the reactive moiety $R_x$. The reactive pairing moiety $R_{px}$ is any suitable reactive group configured to react with the respective reactive moiety $R_x$. In one non-limiting example, one suitable reactive pairing moiety $R_{px}$ may be an alkyne and the reactive moiety $R_x$ may be an azide. The reactive pairing moiety $R_{px}$ may alternatively be an azide moiety and the respective reactive moiety $R_x$ may be alkyne. In other embodiments, the reactive pairing moiety $R_{px}$ may be an active ester functionality and the reactive moiety $R_x$ may be an amino group. In other embodiments, the reactive pairing moiety $R_{px}$ may be aldehyde and the reactive moiety $R_x$ may be amino. Other reactive moiety-reactive pairing moiety combinations are possible, and these examples are in no way limiting.

The moiety configured to reduce surface fouling and/or prevent or reduce cell sticking to the surface the microfluidic device of the moiety-containing reagent of Formula 5 may include any of the moieties described herein, including alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The moiety configured to reduce surface fouling and/or prevent or reduce cell sticking to the surface the microfluidic device of the moiety-containing reagent of Formula 5 may be directly connected (i.e., L', where m=0) or indirectly connected to the reactive pairing moiety $R_{px}$. When the reactive pairing moiety $R_{px}$ is connected indirectly to the moiety configured to reduce surface fouling and/or prevent or reduce cell sticking, the reactive pairing moiety $R_{px}$ may be connected to a linker L' (m=1). The reactive pairing moiety $R_{px}$ may be connected to a first end of the linker L', and the moiety configured to reduce surface fouling and/or prevent or reduce cell sticking may be connected to a second end of the linker L'. Linker L' may have a linear portion wherein a backbone of the linear portion includes 1 to 100 non-hydrogen atoms selected from of any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L' may have one or more arylene, heteroarylene, or heterocyclic groups interrupting the backbone of the linker L'. In some embodiments, the backbone of the linker L' may include 10 to 20 atoms. In other embodiments, the backbone of the linker L' may include about 5 atoms to about 100 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety-containing reagent (Formula 5) reacts with the surface having a surface modifying ligand (Formula 3), a substrate having a conditioned surface of Formula 2 is formed. Linker L' and linker L" then are formally part of linker L, and the reaction of the reactive pairing moiety $R_{px}$ with the reactive moiety $R_x$ yields the coupling group CG of Formula 2.

Surface Modifying Reagent.

The surface modifying reagent is a compound having a structure LG-(L")$_j$-R$_x$ (Formula 4). The linking group LG links covalently to the oxides of the surface of the substrate. The substrate may be a DEP-configured substrate and may include silicon or alumina or hafnium oxide, and oxides may be present as part of the native chemical structure of the substrate or may be introduced as discussed herein. The linking group LG may be any linking group described herein, such as a siloxy or phosphonate ester group, formed from the reaction of a siloxane or phosphonic acid group with the oxide on the surface of the substrate. The reactive moiety $R_x$ is described above. The reactive moiety $R_x$ may be connected directly (L", j=0) or indirectly via a linker L" (j=1) to the linking group LG. The linking group LG may be attached to a first end of the linker L" and the reactive moiety $R_x$ may be connected to a second end of the linker L", which will be distal to the surface of the substrate once the surface modifying reagent has been attached to the surface as in Formula 6.

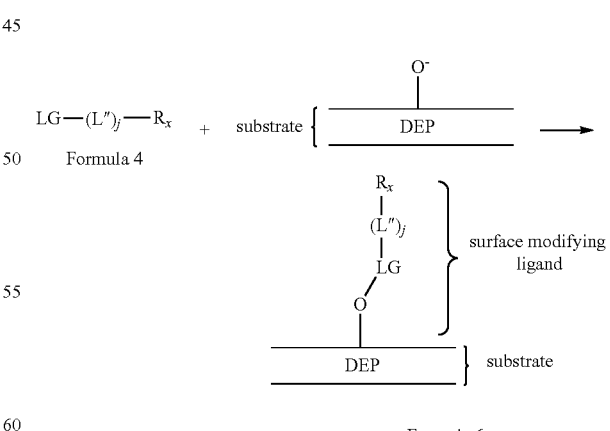

Formula 6

Linker L" may have a linear portion wherein a backbone of the linear portion includes 1 to 100 non-hydrogen atoms selected from of any combination of silicon, carbon, nitrogen, oxygen, sulfur and phosphorus atoms. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker L". In some embodiments, the backbone of the linker L" may include 10 to 20 atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

In some embodiments, the coating material (or surface modifying ligand) is deposited on the inner surfaces of the microfluidic device using chemical vapor deposition. Through chemical vapor deposition, the coating material can achieve densely-packed monolayers in which the molecules comprising the coating material are covalently bonded to the molecules of the inner surfaces of the microfluidic device. To achieve a desirable packing density, molecules comprising, for example, alkyl-terminated siloxane can be vapor deposited at a temperature of at least 110° C. (e.g., at least 120° C., 130° C., 140° C., 150° C., 160° C., etc.), for a period of at least 15 hours (e.g., at least 20, 25, 30, 35, 40, 45, or more hours). Such vapor deposition is typically performed under vacuum and in the presence of a water source, such as a hydrated sulfate salt (e.g., MgSO4.7H20). Typically, increasing the temperature and duration of the vapor deposition produces improved characteristics of the hydrophobic coating material.

The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate). For example, such pre-cleaning can include a solvent bath, such as an acetone bath, an ethanol bath, or a combination thereof. The solvent bath can include sonication. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). The oxygen plasma cleaner can be operated, for example, under vacuum conditions, at 100 W for 60 seconds. Alternatively, liquid-phase treatments, which include oxidizing agents such as hydrogen peroxide to oxidize the surface, may be used in place of an oxygen plasma cleaner. For example, a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Deposition of a coating material comprising a densely-packed monolayer on a fully-assembled microfluidic circuit 120 may be beneficial in providing various functional properties. Without intending to be limited by theory, depositing such a coating material on a fully-assembled microfluidic circuit 120 may be beneficial in preventing delamination caused by a weakened bond between the microfluidic circuit material 116 and the electrode activation substrate 206/dielectric layer and/or the cover 110.

FIGS. 4A-4D depict cross-sectional views of microfluidic devices 500 comprising exemplary classes of coating materials. As illustrated, the coating materials 529 (shown schematically) can comprise a monolayer of densely-packed molecules covalently bound to both the inner surface 508 of the substrate 504 and the inner surface 509 of the cover 510 of the microfluidic device 500. The coating material 529 can be disposed on all inner surfaces 508, 509 proximal to, and facing inwards towards, the enclosure 502 of the microfluidic device 500, including, in some embodiments and as discussed above, the surfaces of microfluidic circuit material (not shown) used to define circuit elements and/or structures within the microfluidic device 500. In alternate embodiments, the coating material 529 can be disposed on only one or some of the inner surfaces of the microfluidic device 500.

Figure 5:
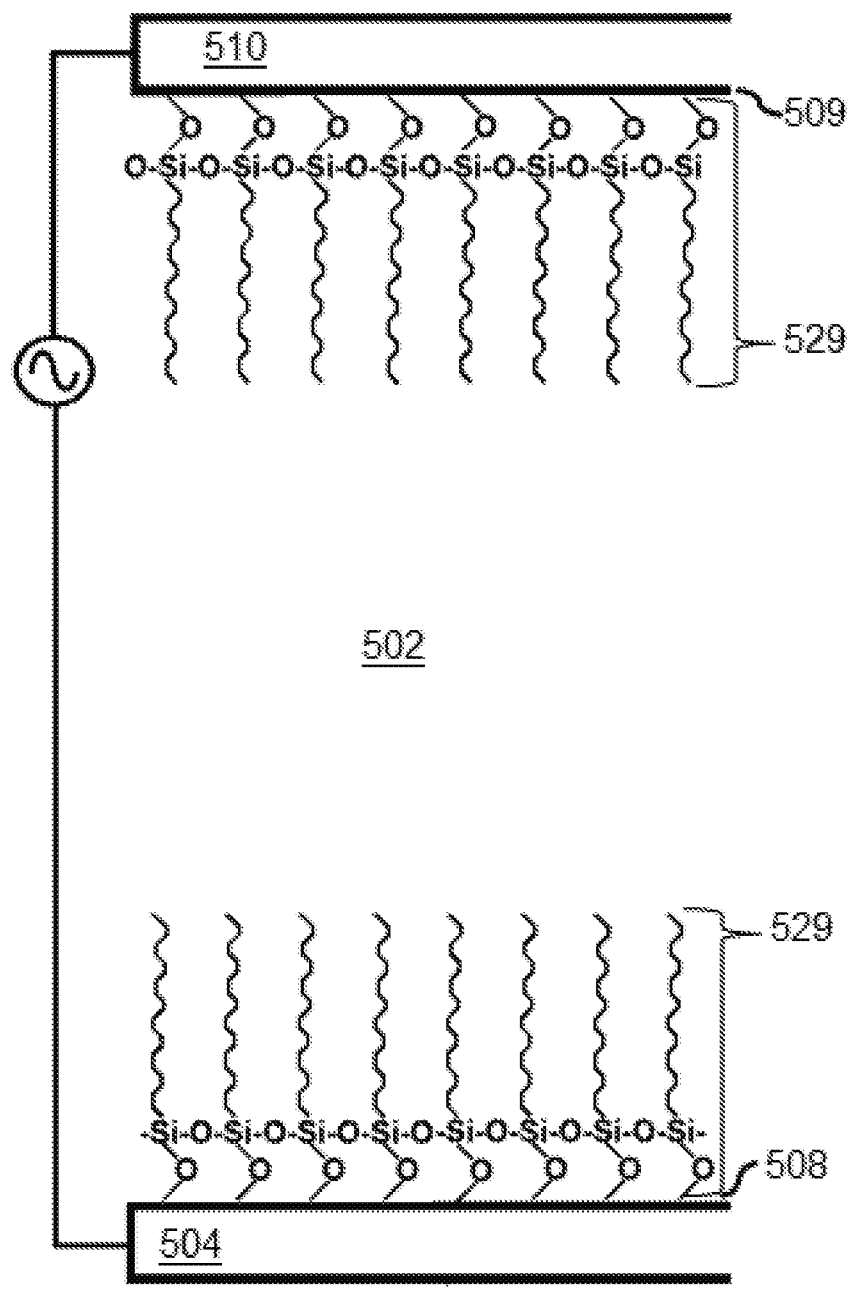
FIG. 5 shows an embodiment of a microfluidic device having a coating material that is covalently bound to the inner surface of both the substrate and the device cover.

In the embodiment shown in FIG. 5, the coating material 529 comprises a monolayer of alkyl-terminated siloxane molecules, each molecule covalently bonded to the inner surfaces 508, 509 of the microfluidic device 500 via a siloxy group. However, any of the above-discussed coating materials 529 can be used (e.g. alkyl-terminated phosphonate ester molecules). More specifically, the alkyl group can comprise a linear chain of at least 10 carbon atoms (e.g. 10, 12, 14, 16, 18, 20, 22, or more carbon atoms) and, optionally, may be a substituted alkyl group. As discussed above, coating materials 529 that comprise a monolayer of densely-packed molecules can have beneficial functional characteristics for use in DEP configured microfluidic devices 500, such as minimal charge trapping, reduced physical/electrical thickness, and a substantially uniform surface.

In some embodiments, the coating material 529 used to coat the inner surface(s) 508, 509 of the microfluidic device 500 provides a functional benefit of reducing cell adhesion. In a specific embodiment, the coating material 529 can comprise a fluoroalkyl group (e.g. a fluorinated alkyl group or a perfluorinated alkyl group) at its enclosure-facing terminus (i.e. the portion of the monolayer of the coating material 529 that is not bound to the inner surfaces 508, 509 and is proximal to the enclosure 502). As discussed above, the coating material 529 can comprise a monolayer of fluoroalkyl-terminated siloxane or fluoroalkyl-terminated phosphonate ester, wherein the fluoroalkyl group is present at the enclosure-facing terminus of the coating material 529. Such a coating material 529 provides a functional benefit in reduced fouling and, more generally, reduced adhesion of biological molecules such as those present on the outer membranes of cells.

In some embodiments, the coating material 529 used to coat the inner surfaces 508, 509 of the microfluidic device 500 provides a functional benefit in presenting one or more moieties that can bind a blocking agent in a blocking solution. Depending on the embodiment, the coating material 529 may comprise or be chemically modified (e.g. by reaction) to present a moiety comprising a cation ("cationic moiety") (e.g. a quaternary ammonium group) at its enclosure-facing terminus. In some embodiments, the coating material 529 may comprise or be chemically modified to present a moiety comprising an anion ("anionic moiety"), such as a phosphonic acid, carboxylic acid, or sulfonic acid moiety, at its enclosure-facing terminus. In some embodiments the coating material 529 may comprise or be chemically modified to present a mixture of cations and anions at its enclosure-facing termini.

Creating Inventories.

Figure 7:
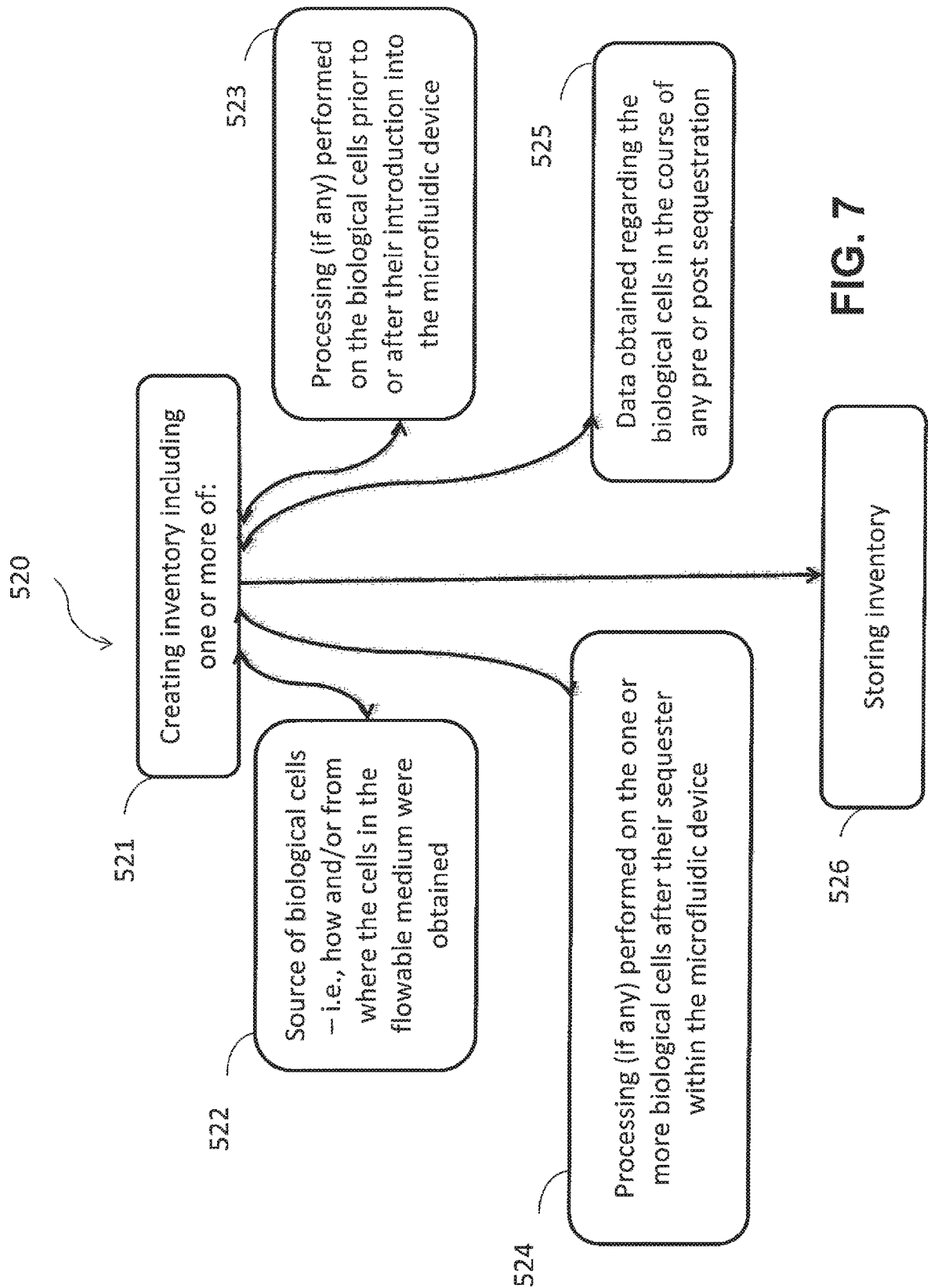
FIG. 7 is a schematic flow diagram of an exemplary method of creating and storing an inventory of biological cells sequestered in a microfluidic device.

Referring again to FIG. 6, although it is not essential for practicing the disclosed methods, prior to freezing the microfluidic device, at (optional) step 520, an inventory of the contents of the microfluidic device is created and stored for future retrieval and reference. For example, and with additional reference to FIG. 7, the inventory 521 can include a basic identity 522 and isolation region location for each of the one or more sequestered cells. The identity of the sequestered cells can include an origin of the cells, in particular, the origin of a sample from which the cells were obtained. This may be, for example, as little information as a sample number (e.g., a patient/subject sample number) and/or an arbitrary label designating each cell sequestered from the sample. Additionally or alternatively, the "identity" of the cells can include the identity of the specific anatomical location from which the cells were collected from the subject, as well as information regarding how the sample from which the cells originated may have been processed prior to introduction of the cells into the microfluidic device. Such sample processing might include dissociating the cells from a tissue sample, such as a tissue biopsy or fine needle aspirate (FNA), or collecting/concentrating the cells from a sample of bodily fluid, such as blood, urine, saliva, semen, buccal swab, synovial fluid, aqueous humour, vitreous humour, tissue culture (e.g., embryos fertilized in culture), etc. Notably, the subject from whom the cell sample was obtained need not be human. For example the cell identification may indicate that the subject was a non-human mammal or other animal (e.g., a lab animal, a domesticated pet, a domesticated farm animal, a zoo animal, a wild animal, etc.).

Additional information that may be included in the inventory (or "library") 521 of the sequestered biological cells includes processes 523 and 524, if any, that were performed on the one or more sequestered biological cells before (523) or after (524) their sequestration within the microfluidic device; and any data 525 obtained in the course of any such pre- or post-sequestration processing. The inventory or library 521 of the sequestered cells is then stored (at step 526) in a memory associated with the microfluidic device. For example, the microfluidic device may include identifying indicia, such as a barcode, sticker, RFID, or the like, and the device inventory may be stored in a database that references the identifying indicia for the device. Alternatively or additionally, the device inventory may be stored in a memory chip (e.g., an EEPROM or the like) coupled to, i.e., and frozen with, the microfluidic device.

In various embodiments, indicated as optional step 530 in FIG. 6, the method further includes (prior to freezing the device) introducing a cell preservation reagent, such as dimethyl sulfoxide (DMSO), into the microfluidic device. In one such embodiment, DMSO is introduced into the microfluidic device at a respective concentration and duration selected such that the one or more sequestered biological cells are substantially surrounded by a solution containing about 10% DMSO at the time of freezing the microfluidic device. In one such embodiment, DMSO is introduced into the microfluidic device at a concentration of about 15% to about 25% by volume (depending, e.g., on the ratio of the volume of the flow region to a total volume of the isolation regions), and allowed to diffuse into the one or more isolation regions containing sequestered biological cells. In one such embodiment, DMSO is perfused through the microfluidic device for an amount of time sufficient to achieve a DMSO concentration of about 10% in each of the one or more isolation regions.

Figure 8:
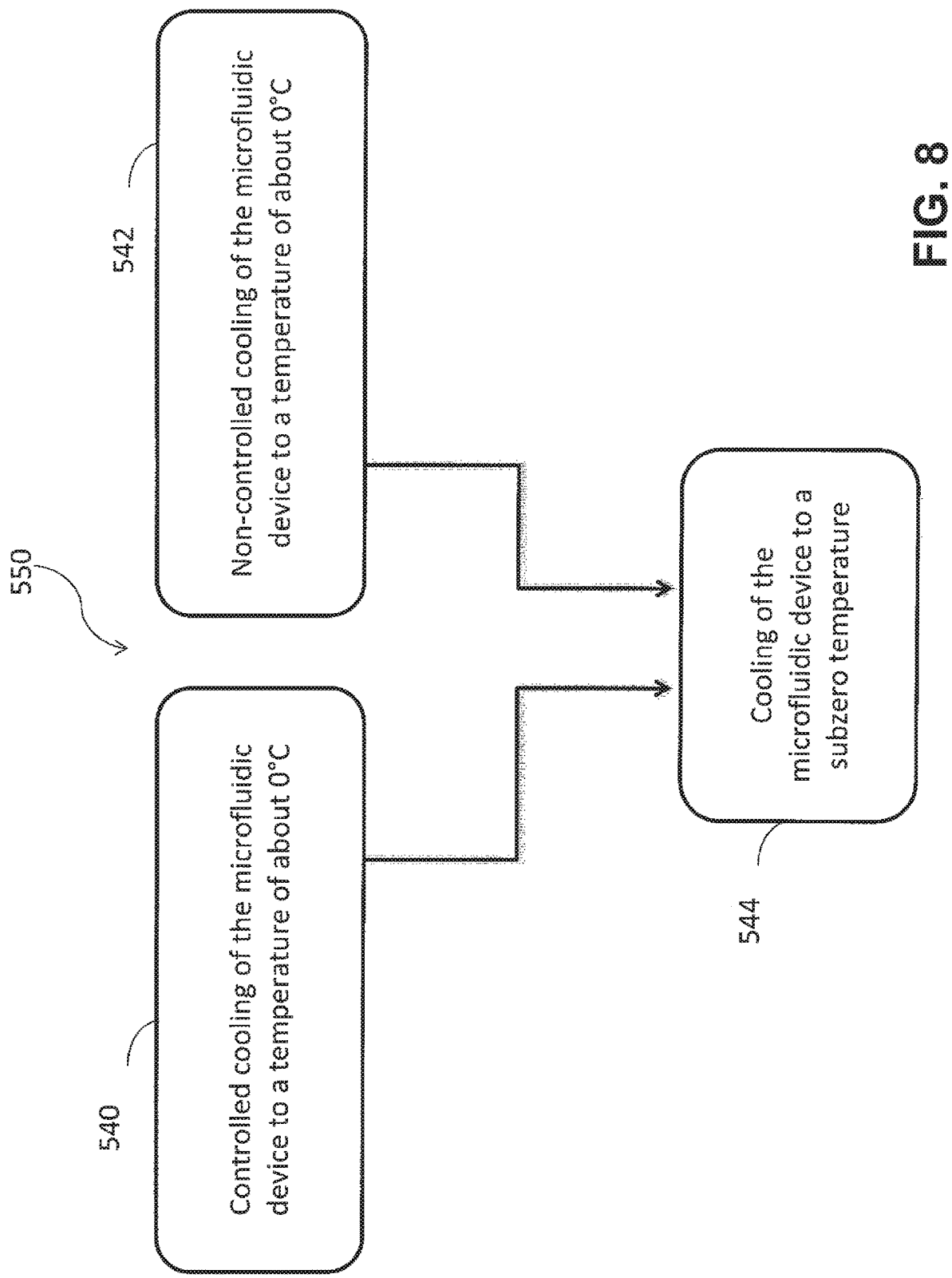
FIG. 8 is a schematic flow diagram of an exemplary method of freezing a microfluidic device including one or more biological cells sequestered therein.

With reference to FIG. 8, freezing the microfluidic device (step 550 in FIG. 6) may include an initial controlled cooling 540 of the microfluidic device to a temperature of near freezing (e.g., about 4° C.) or freezing (e.g., about 0° C.), followed by additional cooling 544 of the microfluidic device to a subzero temperature. Alternatively, the initial cooling may be non-controlled 542. By way of example, and without limitation, the initial controlled cooling 540 of the microfluidic device may be at a rate in a range of about 1° C. per minute to about 2° C. per minute, although a slower rate (e.g., 0.1, 0.2, 0.3, 0.4, 0.5, 0.6, 0.7, 0.8, or 0.9° C. per minute) or faster rate (e.g., 2.1, 2.2, 2.3, 2.4, 2.5, 2.6, 2.7, 2.8, 2.9, 3.0° C. or more per minute) may also be used. The rate of controlled cooling can be varied, depending on the circumstances, for example, in a range from as slow as about 0.1° C. or 0.2° C. per minute, to as fast as about 3.0° C. or 4.0° C. per minute. In various embodiments, the subzero temperature is about −20° C. or less, and more preferably is about −80° C. or less, including in some embodiments about −150° C. or less.

Figure 9:
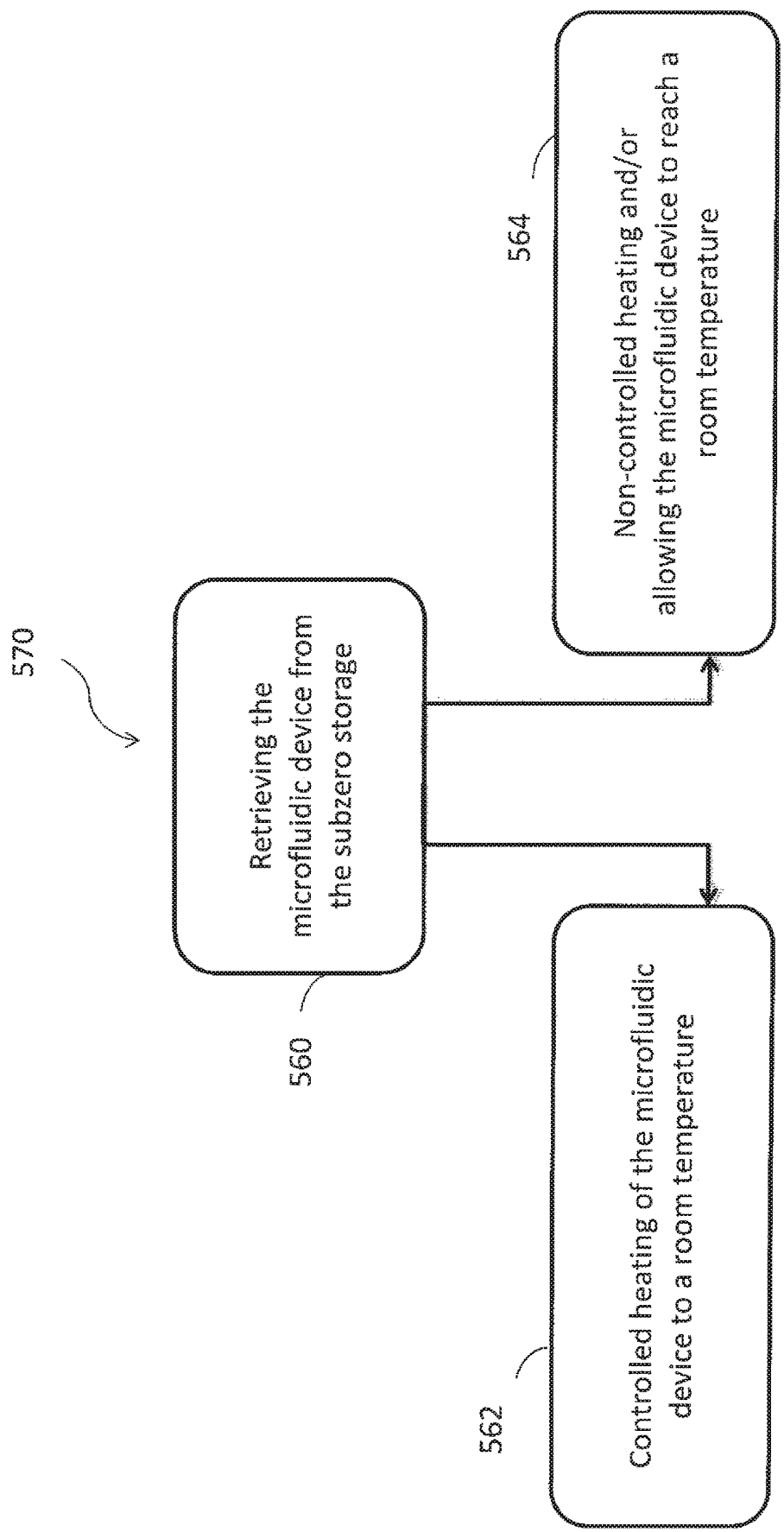
FIG. 9 is a schematic flow diagram of an exemplary method of thawing a frozen microfluidic device including one or more biological cells sequestered therein.

With reference also to FIG. 9, the method may further include thawing the microfluidic device (step 570), including (at step 560), retrieving the microfluidic device from the subzero storage, and then conducting a controlled heating 562 of the microfluidic device and/or allowing the microfluidic device to self-heat to room temperature (step 564), in order to test, evaluate, assay, sequence and/or otherwise use the sequestered cells after thawing. For example, as designated generally by step 590 in FIG. 6, after thawing the microfluidic device, it may be desired to culture one or more viable cells in the microfluidic device, e.g., by continuous or intermittent perfusion of a flowable cell growth medium through the microfluidic device, to thereby generate additional cells therein. In such embodiments, processing of the cells may further include (after thawing) identifying which of the one or more sequestered cells and/or cells generated therefrom are viable after thawing the microfluidic device, and/or retrieving from the microfluidic device at least one sequestered cell and/or cells generated therefrom. By way of example, after thawing, an assay may be performed of one or more cells in the microfluidic device to detect a cell secretion (e.g., an immunological molecule comprising an antibody or a cytokine) or a cell surface marker.

EXAMPLES

Example 1

Freezing 1F5 Hybridoma Cells (ATCC HB-9645) on a Microfluidic Device

The inventors of the present application introduced biological cells grown in a standard culture plate into a microfluidic device at 36° C. The cells were then manipulated and sequestered into respective isolation regions in the microfluidic device (still at 36° C.). A 15% DMSO solution (in medium) was flowed into the microfluidic device, and the device was thereafter incubated at 36° C. for 30 minutes, with no additional perfusion. The microfluidic device was then cooled down to 0° C. at a controlled rate of 1.8° C./minute. It was observed that the sequestered cells continued to move during the freezing process, but slowed down as the temperature decreased. The device was placed in a styrofoam box, which in turn was then placed into −80° C. freezer overnight. The next day, the microfluidic device was removed from freezer (and from the styrofoam box), and allowed to heat top room temperature (assumption is that the device temperature rose to room temp within a minute because of the relatively small device size). The device was then placed onto a testing instrument, with a Peltier set to about 24° C., and perfusion of medium commenced. Thereafter, the temperature of the device was raised to 36° C. at approximately 3° C./minute. It was observed that some cells began moving during the thawing of the device, and that some viable (live) continued to move throughout day, with a small percentage alive at the end of the day, consistent with standard freeze-thaw procedures for biological cells. The OET process continued to work on the microfluidic device (and the cells sequestered therein) after it was frozen and then thawed.

Example 2

Freezing Prostate Cancer Cells on a Microfluidic Device

A tissue biopsy was dissociated into single cells and introduced into a microfluidic device. 12 mL of cell suspension was imported into the device at a concentration of $1 \times 10^6$ cells/mL, the device having a total channel volume of approximately 1.0 mL, with a nominal quantity of cells visible at any one time of approximately 1000 cells. The cells were placed into isolation chambers individually, using an automated penning algorithm. The device temperature was set at 12° C. during the cell loading and isolation process. The microfluidic device was then placed into freezer for a sufficient time to be frozen. The device was then thawed by removal from freezer, and placed on an instrument (at T=12° C.). It was observed that viable cells in the isolation chambers were mobile using OET, and could be exported for further analysis, such as sequencing.

While embodiments have been shown and described, various modifications may be made without departing from the scope of the inventive concepts disclosed herein. The invention(s), therefore, should not be limited, except as defined in the following claims.

What is claimed is:

1. A method of processing and storing biological cells in a microfluidic device comprising a flow region and a plurality of isolation chambers, each isolation chamber comprising an isolation region and a connection region that fluidically connects the isolation region to the flow region, wherein each isolation region comprises a single opening and is an unswept region of the microfluidic device, the method comprising:
   introducing a flowable medium into the flow region of the microfluidic device, the flowable medium including biological cells;
   sequestering one or more biological cells from the flowable medium in the flow region, wherein sequestering comprises moving the one or more biological cells into the isolation region of each of one or more isolation chambers of the microfluidic device; and
   freezing the microfluidic device including the one or more biological cells sequestered therein.

2. The method of claim 1, wherein a single biological cell is sequestered in each of a plurality of isolation regions.

3. The method of claim 1, wherein each isolation region has a volume in a range of about $1.5 \times 10^5$ cubic microns to about $1.5 \times 10^6$ cubic microns.

4. The method of claim 1, further comprising, prior to freezing the microfluidic device, creating an inventory including at least an identity and isolation region location for each of the one or more sequestered biological cells, and storing the inventory in a memory associated with the microfluidic device.

5. The method of claim 4, the inventory further including information identifying one or more of (i) processing, if any, performed on the one or more sequestered biological cells after their sequester within the microfluidic device; and (ii) data obtained in the course of any such pre or post sequestration processing.

6. The method of claim 4, wherein the memory comprises a chip or other device coupled to, and frozen with, the microfluidic device.

7. The method of claim 1, wherein freezing the microfluidic device comprises an initial controlled cooling of the microfluidic device to a temperature of about 0° C., followed by a subsequent cooling of the microfluidic device to a subzero temperature.

8. The method of claim 7, wherein the initial controlled cooling comprises cooling the microfluidic device at a rate in a range of about 0.1° C. per minute to about 2° C. per minute.

9. The method of claim 7, wherein the subzero temperature is about −20° C. or less.

10. The method of claim 1, further comprising, prior to freezing the microfluidic device, introducing a cell preservation reagent into the microfluidic device.

11. The method of claim 10, wherein the cell preservation reagent comprises dimethyl sulfoxide (DMSO).

12. The method of claim 11, wherein the DMSO is either introduced into the microfluidic device at a concentration of about 15% to about 25% by volume and allowed to diffuse into the one or more isolation regions containing sequestered biological cells, or is perfused through the microfluidic device for an amount of time sufficient to achieve a DMSO concentration of about 10% in each of the one or more isolation regions.

13. The method of claim 1, further comprising
   thawing the microfluidic device, wherein thawing the microfluidic device comprises one or both of (i) a controlled heating of the microfluidic device, and (ii) allowing the microfluidic device to self-heat to room temperature, and
   retrieving from the microfluidic device at least one sequestered cell and/or cells generated therefrom.

14. The method of claim 13, further comprising, after thawing the microfluidic device, culturing one or more viable cells in the microfluidic device to thereby generate additional cells therein.

15. The method of claim 1, the one or more sequestered biological cells comprising at least one or more starting cells sequestered in a first isolation region, the method further comprising
   prior to freezing the microfluidic device, culturing the one or more starting cells to generate a plurality of new cells in the first isolation region, the plurality of new cells being adequate in number so that at least one viable cell is located in the first isolation region after thawing the microfluidic device.

16. The method of claim 1, further comprising performing an assay of the one or more sequestered biological cells, wherein the assay is used to detect a cell secretion or a cell surface marker.

17. The method of claim 1, wherein the flow region and one or more isolation regions are treated with a blocking solution to prevent or reduce cell adhesion.

18. The method of claim 1, wherein the microfluidic device comprises an inner substrate surface that comprises a coating material.

19. The method of claim 18, wherein the coating material comprises molecules having a linking group and an alkyl moiety, wherein the linking group is covalently bonded to the inner substrate surface, such that the molecules of the coating material form a densely-packed monolayer structure covalently bound to the inner substrate surface.

20. The method of claim 19, wherein the alkyl moiety is a fluoroalkyl or perfluoroalkyl moiety.

21. The method of claim 19, wherein the linking group is a siloxy linking group.

22. The method of claim 19, wherein the alkyl moiety comprises a linear chain of carbons comprising at least 10 carbon atoms.

23. The method of claim 18, wherein the coating material comprises molecules having a linking group and a cationic moiety and/or an anionic moiety, wherein the linking group is covalently bonded to the inner substrate surface.

24. The method of claim 18, wherein the coating material comprises a polymer covalently bound to the inner substrate surface, the coating material comprising alkylene ether moieties, saccharide moieties, or amino acid moieties.

25. The method of claim 24, wherein the coating material comprises dextran or poly-ethylene glycol.

26. A method of storing and retrieving biological cells from a microfluidic device comprising a flow region and a plurality of isolation chambers, each isolation chamber comprising an isolation region and a connection region that fluidically connects the isolation region to the flow region, wherein each isolation region comprises a single opening and is an unswept region of the microfluidic device, the method comprising:
sequestering one or more biological cells in the flow region, wherein sequestering comprises moving the one or more biological cells into the isolation region of each of one or more isolation chambers of the microfluidic device;
freezing the microfluidic device, including the one or more biological cells sequestered therein, for a period of time;
thawing the microfluidic device; and
retrieving from the microfluidic device at least one sequestered cell and/or cells generated therefrom.

27. The method of claim 1, wherein the flow region comprises a flow channel, and wherein the connection region of each isolation chamber comprises a proximal opening in fluid communication with the flow channel having a width Wcon of about 20 microns to about 100 microns, and a distal opening in fluid communication with the respective isolation region of the isolation chamber, wherein a length Lcon from the proximal opening to the distal opening of the connection region is at least 1.0 times the width Wcon of the proximal opening.

28. The device of claim 27, wherein the length Lcon of the connection region is at least 1.5 times the width Wcon of the proximal opening.

29. The device of claim 27, wherein the length Lcon of the connection region is at least 2.0 times the width Wcon of the proximal opening.

30. The device of claim 27, wherein the width Wcon of the proximal opening of each connection region is in a range from about 20 microns to about 60 microns.

31. The device of claim 27, wherein the length Lcon of the connection region is in a range from about 20 microns to about 500 microns.

32. The device of claim 27, wherein a width of the flow channel is in a range from about 50 microns to about 500 microns.

33. The device of claim 27, wherein a height of the flow channel is in a range from about 20 microns to about 100 microns.

34. The device of claim 27, wherein a volume of each isolation region is in a range from about $2 \times 10^4$ cubic microns to about $2 \times 10^6$ cubic microns.

* * * * *